(12) United States Patent  
Gaudilliere et al.

(10) Patent No.: US 6,894,057 B2  
(45) Date of Patent: May 17, 2005

(54) OXO-AZABICYCLIC COMPOUNDS

(75) Inventors: Bernard Gaudilliere, Nanterre (FR); Henry Jacobelli, Paray Vieille Poste (FR); Catherine Kostlan, Saline, MI (US); Jack Jie Li, Ann Arbor, MI (US); Wen-Song Yue, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 20 days.

(21) Appl. No.: 10/384,115

(22) Filed: Mar. 7, 2003

(65) Prior Publication Data

US 2003/0216402 A1 Nov. 20, 2003

Related U.S. Application Data

(60) Provisional application No. 60/362,994, filed on Mar. 8, 2002.

(30) Foreign Application Priority Data

Mar. 8, 2002 (WO) ................. PCT/EP02/03240

(51) Int. Cl.$^7$ .................. C07D 239/91; C07D 471/04; A61K 31/5025
(52) U.S. Cl. .................... 514/264.1; 544/279
(58) Field of Search ............. 544/279; 514/264.1

(56) References Cited

U.S. PATENT DOCUMENTS

| | | | |
|---|---|---|---|
| 4,818,819 A | 4/1989 | Taylor et al. | 544/279 |
| 4,902,796 A | 2/1990 | Taylor et al. | 544/279 |
| 5,389,631 A | 2/1995 | Claremon et al. | |
| 5,646,141 A | 7/1997 | Varney et al. | 514/222.8 |
| 5,925,642 A * | 7/1999 | Ulrich | 514/258 |
| 5,929,097 A | 7/1999 | Levin et al. | 514/351 |

(Continued)

FOREIGN PATENT DOCUMENTS

| | | |
|---|---|---|
| EP | 0935963 | 8/1999 |
| EP | 1138680 | 10/2001 |
| JP | 10195063 A | 7/1998 |
| JP | 10195063 | 7/1998 |
| WO | 9616046 | 5/1996 |
| WO | 9816514 | 4/1998 |

(Continued)

OTHER PUBLICATIONS

Ramussen et al., Matrix Metalloproteinase Inhibition as a Novel Anticancer Strategy, Pharmacol. Ther. vol. 75, No. 1, pp. 69–75, 1997.*

Chambers et al., Review: Changing Views of the Role of Matrix Metalloproteinases in Metastasis, Journal of the National Cancer Institute, vol. 89, No. 17, pp. 1260–1270, Sep. 1997.*

(Continued)

*Primary Examiner*—Deepak Rao
(74) *Attorney, Agent, or Firm*—Pfizer Inc.; Pamela C. Ancona; Claude F. Purchase, Jr.

(57) ABSTRACT

A compound selected from those of formula (I):

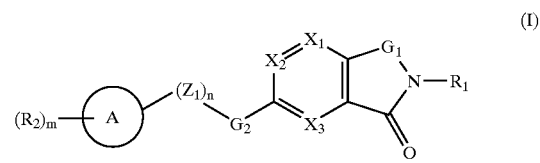

wherein:

$X_1$, $X_2$, and $X_3$, represent N or —$CR_3$ in which $R_3$ is as described in the description, $G_1$ represents a group selected from those of formulae (i/a) and (i/b):

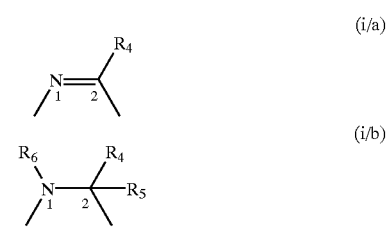

in which $R_4$, $R_5$, and $R_6$ are as defined in the description, $G_2$ represents a group selected from carbon—carbon triple bond, —CH═C═CH—, C═O, C═S, S(O)$_{n1}$ in which n1 represents an integer from 0 to 2 inclusive, or a group of formula (i/c):

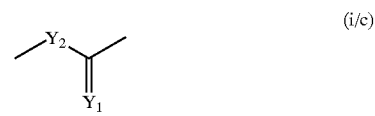

in which $Y_1$ represents O, S, —NH or -Nalkyl, and $Y_2$ represents O, S, —NH or -Nalkyl, n is an integer from 0 to 6 inclusive, and m is an integer from 0 to 7 inclusive, $Z_1$ represents —$CR_9R_{10}$, wherein $R_9$ and $R_{10}$ are as defined in the description, A represents a ring system, $R_1$ represents a group selected from H, alkyl, alkenyl, alkynyl, optionally substituted and the group of formula (i/d):

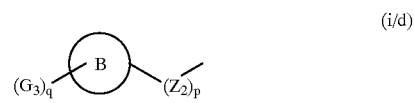

in which p, $Z_2$, B, q and $G_3$ are as defined in the description and optionally, its optical isomers, N-oxide, and addition salts thereof with a pharmaceutically-acceptable acid or base, and medicinal products containing the same are useful as specific inhibitors of type-13 matrix mettaloprotease.

17 Claims, No Drawings

U.S. PATENT DOCUMENTS

| | | | |
|---|---|---|---|
| 5,948,780 A | 9/1999 | Peterson, Jr. et al. | 514/255 |
| 6,008,243 A | 12/1999 | Bender et al. | 514/422 |
| 6,225,311 B1 | 5/2001 | Levin et al. | 514/227.5 |
| 2002/0151555 A1 | 10/2002 | Barvian et al. | 514/256 |
| 2002/0151558 A1 | 10/2002 | Andrianjara et al. | 514/267 |
| 2002/0156061 A1 | 10/2002 | Barvian et al. | 514/183 |
| 2002/0156069 A1 | 10/2002 | Picard et al. | 514/223.2 |
| 2002/0161000 A1 | 10/2002 | Barvian et al. | 514/217.04 |
| 2003/0130278 A1 | 7/2003 | Gaudilliere et al. | |
| 2003/0144274 A1 | 7/2003 | Bunker et al. | |
| 2003/0216402 A1 | 11/2003 | Gaudilliere et al. | |
| 2003/0220355 A1 | 11/2003 | Gaudilliere et al. | |
| 2004/0006077 A1 | 1/2004 | Gaudilliere et al. | |
| 2004/0034009 A1 | 2/2004 | Roark | |
| 2004/0034054 A1 | 2/2004 | Wilson | |
| 2004/0038959 A1 | 2/2004 | Bunker et al. | |
| 2004/0038960 A1 | 2/2004 | Li | |
| 2004/0038961 A1 | 2/2004 | Bunker et al. | |
| 2004/0038973 A1 | 2/2004 | Nahra et al. | |
| 2004/0038974 A1 | 2/2004 | Ortwine | |
| 2004/0038994 A1 | 2/2004 | Wilson | |
| 2004/0039012 A1 | 2/2004 | Wilson | |
| 2004/0043983 A1 | 3/2004 | Li | |
| 2004/0043984 A1 | 3/2004 | O'Brien | |
| 2004/0043985 A1 | 3/2004 | Hicks et al. | |
| 2004/0043986 A1 | 3/2004 | Nahra et al. | |
| 2004/0043991 A1 | 3/2004 | Picard et al. | |
| 2004/0044000 A1 | 3/2004 | Bunker et al. | |
| 2004/0063673 A1 | 4/2004 | Johnson | |
| 2004/0142950 A1 | 7/2004 | Bunker et al. | |

FOREIGN PATENT DOCUMENTS

| | | |
|---|---|---|
| WO | 9826664 | 6/1998 |
| WO | 0009485 | 2/2000 |
| WO | 0035906 | 6/2000 |
| WO | 0040561 | 7/2000 |
| WO | 0044716 | 8/2000 |
| WO | 0045063 | 8/2000 |
| WO | 0112611 | 2/2001 |
| WO | 0155133 | 8/2001 |
| WO | WO 01/55133 A1 | 8/2001 |
| WO | 0163244 | 8/2001 |
| WO | 0206513 | 1/2002 |
| WO | 0234726 | 5/2002 |
| WO | 0234753 | 5/2002 |
| WO | 02064080 | 8/2002 |
| WO | 02064547 | 8/2002 |
| WO | 02064568 | 8/2002 |
| WO | 02064571 | 8/2002 |
| WO | 02064572 | 8/2002 |
| WO | 02064578 | 8/2002 |
| WO | 02064595 | 8/2002 |
| WO | 02064598 | 8/2002 |
| WO | 02064599 | 8/2002 |
| WO | WO03/032999 A1 | 4/2003 |
| WO | WO03/033478 A1 | 4/2003 |
| WO | WO03/076417 A2 | 9/2003 |
| WO | WO04/000322 A1 | 12/2003 |
| WO | WO04/014354 A1 | 2/2004 |
| WO | WO04/014365 A1 | 2/2004 |
| WO | WO04/014375 A2 | 2/2004 |
| WO | WO04/014377 A1 | 2/2004 |
| WO | WO04/014378 A1 | 2/2004 |
| WO | WO04/014379 A1 | 2/2004 |
| WO | WO04/014384 A2 | 2/2004 |
| WO | WO04/014388 A1 | 2/2004 |
| WO | WO04/014389 A1 | 2/2004 |
| WO | WO04/014869 A2 | 2/2004 |
| WO | WO04/014880 A1 | 2/2004 |
| WO | WO04/014908 A1 | 2/2004 |
| WO | WO04/014909 A1 | 2/2004 |
| WO | WO04/014916 A1 | 2/2004 |
| WO | WO04/014921 A1 | 2/2004 |
| WO | WO04/014923 A1 | 2/2004 |
| WO | WO2004/014866 A1 | 2/2004 |

OTHER PUBLICATIONS

Morris et al., PubMed Abstract (Invasion Metastasis 17(6):281–96), 1997.*

Simone, Oncology: Introduction, Cecil Textbook of Medicine, 20th Edition, vol. 1, pp. 1004–1010, 1996.*

E.C. Taylor, et al., "Pteridines. 51. A New and Unequivocal Route to C–6 Carbon–Substituted Pterins and Pteridines", J. Org. Chem. 1987, 52:3997–4000.

E.C. Taylor, et al., "Convergent and Efficient Palladium–Effected Synthesis of 5,10–Dideaza–5,6,7,8–tetrahydrofolic Acid (DDATHF)", J. Org. Chem. 1989, 52:3618–3624.

M.G. Natchus, et al., "Development of New Carboxylic Acid–Based MMP Inhibitors Derived from Functionalized Propargylglycines", Journal of Medicinal Chemistry 2001, 44(7):1060–1071.

Derwent Publication Lt. Abstract No. 2001–514548; XP002213435.

A.B. Dyatkin et al., "The Solid Phase Synthesis of Complex Propargylamines Using the Combination of Sonogashira and Mannich Reactions", Tetrahedron Letters, Elsevier Science Publishers, Amsterdam, NL 1998, 39(22)3647–3650.

John Montana & Andrew Baxter, "The design of selective non–substrate–based matrix metalloproteinase inhibitors", Current Opinion in Drug Discovery & Development 2000, 3(4):353–361.

Clark et al., "Matrix metalloproteinase inhibitors in the treatment of arthritis", Current Opinion in Anti–inflammatory & Immunomodulatory Investigational Drugs 2000, 2(1):16–25.

Chen et al., "Structure–Based Design of a Novel, Potent, and Selective Inhibitor for MMP–13 Utilizing NMR Spectroscopy and Computer–Aided Molecular Design", J. Am. Chem. Soc. 2000, 122:9648–9654.

U.S. Appl. No. 10/634,489, filed Aug. 05, 2003, inventor Roark.

U.S. Appl. No. 10/071,032, filed Feb. 08, 2002, inventor Dyer et al.

Chen, et al., "Structure–Based Design of a Novel, Potent, and Selective Inhibitor for MMP–13 Utilizing NMR Spectroscopy and Computer–Aided Molecular Design", J. Am. Chem. Soc. 2000, 122–9648–9654.

Lovejoy, et al., "Crystal structures of MMP–1 and –13 reveal the structural basis for selectivity of collagenase inhibitors", Nature Structural Biol., 1999; 6:217–221.

Moy, et al., High–resolution solution structure of the catalytic fragment of human collagenase–3 (MMP–13) complexed with a hydroxamic acid inhibitor, J. Mol. Biol., 2000; 302, 671–689.

Mitchell, et al., "Cloning, Expression, and Type II Collagenolytic Activity of Matrix Metalloproteinase–13 from Human Osteoarthritic Cartilage", J. Clin. Invest., 1996; 97(3):761–768.

Neuhold, et al., "Postnatal expression in hyaline cartilage of constitutively active human collagenase–3 (MMP–13) induces osteoarthritis in mice", J. Clin. Invest., 2001;107: 35–44.

Dahlberg, et al., Selective Enhancement of Collagenase–Mediated Cleavage of Resident Type II Collagen in Cultured Osteoarthritic Cartilage and Arrest with a Synthetic Inhibitor that Spares Collagenase I (Matrix Metalloproproteinase I) Arthrit & Rheum 2000–A3(3): 673–682.

Billinghurst, et al., "Comparison of the Degradiation of Type II Collagen and Proteoglycan in Nasal and Articular Cartilages Induced by Interleuken–1 and the Selective Inhibition of Type II Collagen Cleavage by Collagenase", Arthrit & Rheum., 2000; 43(3): 664–672.

Billinghurst, et al., "Enhanced Cleavage of Type II Collagen by Collagenase in Osteoarthritic Articular Cartilage", J. Clin. Invest., 1997; 99:1534–1545.

Hirota, et al., "Novel Synthesis of Pyrido[3,4–d]pyrimidines, Pyrido[2,3–d]–pyrimidines, and Quinazolines via Palladium–Catalyzed Oxidative coupling", Heterocycles, 1994; 37(1):563–570.

* cited by examiner

OXO-AZABICYCLIC COMPOUNDS

CROSS-REFERENCE TO RELATED APPLICATIONS

This patent application claims benefit of priority from U.S. provisional Patent Application No. 60/362,994, filed Mar. 8, 2002, and PCT International Patent Application no. PCT/EP02/03240, filed Mar. 8, 2002.

FIELD OF THE INVENTION

The present invention relates to novel oxo azabicyclic compounds which are useful for preparing medicinal products for treating complaints involving a therapy with a matrix metalloprotease-13 (MMP-13) inhibitor. These medicinal products are useful in particular for treating certain inflammatory conditions such as rheumatoid arthritis or osteoarthritis, as well as certain proliferative conditions such as cancers, particularly human breast cancer.

TECHNOLOGICAL BACKGROUND OF THE INVENTION

Matrix metalloproteases (MMPs) are enzymes which are involved in the renewal of extracellular matrix tissue, such as cartilage, tendons and joints. MMPs bring about the destruction of the extracellular matrix tissue, which is compensated for, in a non-pathological physiological state, by its simultaneous regeneration.

Under normal physiological conditions, the activity of these extremely aggressive peptidases is controlled by specialized proteins which inhibit MMPs, such as the tissue inhibitors of metalloprotease (TIMPs).

Local equilibrium of the activities of MMPs and of TIMPs is critical for the renewal of the extracellular matrix. Modifications of this equilibrium which result in an excess of active MMPs, relative to their inhibitor, induce a pathological destruction of cartilage, which is observed in particular in rheumatoid arthritis and in osteoarthritis.

In pathological situations, an irreversible degradation of articular cartilage takes place, as is the case in rheumatic diseases such as rheumatoid arthritis or osteoarthritis. In these pathologies, the cartilage degradation process predominates, leading to a destruction of the tissue and resulting in a loss of function.

At least twenty different matrix metalloproteases have been identified to date and are subdivided into four groups, the collagenases, the gelatinases, the stromelysins and the membrane-type MMPs (MT-MMPs), respectively.

Matrix metalloprotease-13 (MMP-13) is a collagenase-type MMP which constitutes the predominant collagenase observed during osteoarthritis, in the course of which pathology the chondrocyte directs the destruction of cartilage.

There is a need for novel MMP inhibitors, more particularly for MMP-13 inhibitors, in order to prevent and/or correct the imbalance in the renewal of extracellular matrix tissue, such as arthritis, rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases (COPD), age-related macular degeneration (ARMD) and cancer.

MMP-inhibitor compounds are known. Most of these MMP-inhibitors are not selective for a single MMP, such as those described by Montana and Baxter (2000) or by Clark et al. (2000).

There is also a need in the prior art for novel inhibitors that are active on matrix metalloprotease-13, in order to enrich the therapeutic arsenal that can be used for treating pathologies associated with the destruction of the extracellular matrix and with cancer.

The patent application WO9826664 describes quinazolinone compounds which are used as new antifungic compounds.

The compounds of the present application are novel and represent powerful inhibitors of MMP-13. They are consequently of use in the treatment of rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases (COPDs), age-related degeneration (ARMD) and cancer.

SUMMARY OF THE INVENTION

The applicant has identified novel oxo azabicyclic compounds that are matrix metalloprotease inhibitors, and more specifically compounds that are selective MMP-13 inhibitors.

More specifically, the present invention relates to compounds of formula (I):

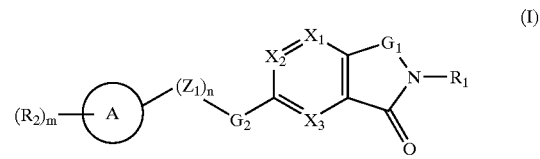

wherein:

$X_1$, $X_2$, and $X_3$, independently of each other, represent a nitrogen atom or a group —$CR_3$ in which $R_3$ represents a group selected from hydrogen, ($C_1$–$C_6$)alkyl, amino, mono($C_1$–$C_6$)alkylamino, di($C_1$–$C_6$)alkylamino, hydroxy, ($C_1$–$C_6$)alkoxy, and halogen, with the proviso that not more than two of the groups $X_1$, $X_2$ and $X_3$ simultaneously represent a nitrogen atom, $G_1$ represents a group selected from those of formulae (i/a) and (i/b):

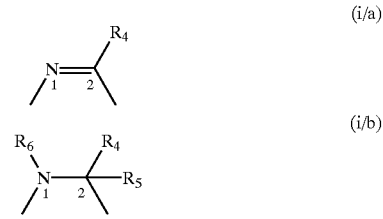

in which:
the carbon atom with number 2 is attached to the group N—$R_1$ in the ring,
$R_4$ and $R_5$, identical or different, independently of each other, represent a group selected from hydrogen, ($C_1$–$C_6$)alkyl, aryl, aryl($C_1$–$C_6$)alkyl, cycloalkyl, cycloalkyl($C_1$–$C_6$)alkyl, heteroaryl, heteroaryl($C_1$–$C_6$)alkyl, heterocycloalkyl, and heterocycloalkyl($C_1$–$C_6$)alkyl,
$R_6$ represents a group selected from:
hydrogen, trifluoromethyl, $OR_7$, $NR_7R_8$, in which $R_7$ and $R_8$, identical or different independently of each other, represent hydrogen or ($C_1$–$C_6$)alkyl, ($C_1$–$C_6$)alkyl, ($C_2$–$C_6$)alkenyl, ($C_2$–$C_6$)alkynyl, aryl, aryl($C_1$–$C_6$)alkyl, cycloalkyl($C_1$–$C_6$)alkyl, heteroaryl, heteroaryl($C_1$–$C_6$)alkyl, heterocycloalkyl, and heterocycloalkyl($C_1$–$C_6$) alkyl, these groups being optionally substituted by one or more groups, which may be identical or different independently of each other, selected from halogen, amino, mono($C_1$–$C_6$)alkylamino, di($C_1$–$C_6$)alkylamino, each alkyl moiety being identical or different independently of each other, cyano, trihalogeno($C_1$–$C_6$)alkyl, ($C_1$–$C_6$)acyl, —C(=O)O$R_7$, —O$R_7$ and —S$R_7$, in which $R_7$ is as defined hereinbefore, $G_2$ represents a group selected from carbon—carbon triple bond, —CH=C=CH—, C=O, C=S, S(O)$_{n1}$ in which n1 represents an integer from 0 to 2 inclusive, and a group of formula (i/c):

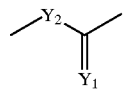

(i/c)

in which the carbon atom with number 1 is attached to the bicycle of the compound of formula (I), $Y_1$ represents a group selected from oxygen, sulphur, —NH and —N($C_1$–$C_6$)alkyl, and $Y_2$ represents a group selected from oxygen, sulphur, —NH and —N($C_1$–$C_6$)alkyl, n represents an integer from 0 to 6 inclusive, $Z_1$ represents —C$R_9R_{10}$, wherein $R_9$ and $R_{10}$, identical or different independently of each other, represent a group selected from hydrogen, ($C_1$–$C_6$)alkyl, trihalogeno ($C_1$–$C_6$)alkyl, halogen, —O$R_7$, —S$R_7$, and —C(=O) O$R_7$, in which $R_7$ is as defined hereinbefore, amino, mono($C_1$–$C_6$)alkylamino, di($C_1$–$C_6$)alkylamino in which each alkyl moiety is identical or different independently of each other, and wherein when n is greater than or equal to 2, the hydrocarbon chain $Z_1$ optionally contains one to two isolated or conjugated multiple bonds, and/or wherein when n is greater than or equal to 2, one of said —C$R_9R_{10}$ may optionally be replaced with a group selected from oxygen, S(O)$_{n1}$ in which n1 is as defined hereinbefore, —NH and —N($C_1$–$C_6$)alkyl, A represents a group selected from aryl, heteroaryl, cycloalkyl, and heterocycloalkyl, these groups being 5- or 6-membered monocycle or bicycle composed of two 5- or 6-membered monocycle, $R_1$ represents a group selected from:
hydrogen,
($C_1$–$C_6$)alkyl, ($C_2$–$C_6$)alkenyl, ($C_2$–$C_6$)alkynyl, these groups may be optionally substituted with one or more groups, which may be identical or different independently of each other, selected from amino, cyano, trihalogeno($C_1$–$C_6$)alkyl, cycloalkyl, —C(=O)N$R_7R_8$, —C(=O)O$R_8$, O$R_8$, S$R_8$, in which $R_7$ and $R_8$, which may be identical or different independently of each other, represent hydrogen or ($C_1$–$C_6$)alkyl, and the group of formula (i/d):

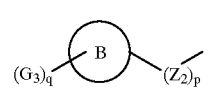

(i/d)

in which p is an integer from 0 to 8 inclusive, $Z_2$ represents —C$R_{11}R_{12}$ wherein $R_{11}$ and $R_{12}$, identical or different independently of each other, represent a group selected from hydrogen, ($C_1$–$C_6$)alkyl, phenyl, trihalogeno($C_1$–$C_6$)alkyl, halogen, amino, O$R_7$, S$R_7$ and —C(=O)O$R_7$ in which $R_7$ represents hydrogen or ($C_1$–$C_6$)alkyl, and wherein when p is greater than or equal to 2, the hydrocarbon chain $Z_2$ optionally contains one or two isolated or conjugated multiple bonds, and/or wherein n is greater than or equal to 2, one of said —C$R_{11}R_{12}$ may optionally be replaced with a group selected from oxygen, S(O)$_{n1}$ in which n1 is as defined hereinbefore, —NH, —N($C_1$–$C_6$)alkyl, and carbonyl, B represents a group selected from aryl, heteroaryl, cycloalkyl, and heterocycloalkyl, these groups being 5- or 6-membered monocycle or bicycle composed of two 5- or 6-membered monocycle, q is an integer from 0 to 7 inclusive, the group(s) $G_3$, which may be identical or different independently of each other, is (are) selected from ($C_1$–$C_6$)alkyl, halogen, CN, NO$_2$, CF$_3$, OCF$_3$, —(CH$_2$)$_k$N$R_{13}R_{14}$, —N($R_{13}$)C(=O)$R_{14}$, —N($R_{13}$)C(=O)O$R_{14}$, —N($R_{13}$)SO$_2R_{14}$, —N(SO$_2R_{13}$)$_2$, —O$R_{13}$, —S(O)$_{k1}R_{13}$, —SO$_2$—N($R_{13}$)—(CH$_2$)$_{k2}$—N$R_{14}R_{15}$, —(CH$_2$)$_k$SO$_2$N$R_{13}R_{14}$, —$X_4$(CH$_2$)$_k$C(=O)O$R_{13}$, —(CH$_2$)$_k$C(=O)O$R_{13}$, —C(=O)O—(CH$_2$)$_{k2}$—N$R_{13}R_{14}$, —C(=O)O—(CH$_2$)$_{k2}$—C(=O)O$R_{16}$, —$X_4$(CH$_2$)$_k$C(=O)N$R_{13}R_{14}$, —(CH$_2$)$_k$C(=O)N$R_{13}R_{14}$, —$R_{17}$—C(=O)O$R_{13}$, -$X_5$—$R_{18}$, and —C(=O)—$R_{19}$—N$R_{13}R_{14}$ in which:

$X_4$ represents a group selected from oxygen atom, sulphur atom optionally substituted by one or two oxygen atoms, and nitrogen atom substituted by a hydrogen atom or a ($C_1$–$C_6$)alkyl group, k is an integer from 0 to 3 inclusive, k1 is an integer from 0 to 2 inclusive, k2 is an integer from 1 to 4 inclusive, $R_{13}$, $R_{14}$ and $R_{15}$, which may be identical or different independently of each other, are selected from hydrogen and ($C_1$–$C_6$)alkyl, $R_{16}$ represents a group selected from ($C_1$–$C_6$)alkyl, —$R_{19}$—N$R_{13}R_{14}$, —$R_{19}$—N$R_{13}$—C(=O)—$R_{19}$—N$R_{14}R_{15}$, and —C(=O)O—$R_{19}$—N$R_{13}R_{14}$ in which $R_{19}$ represents a linear or branched ($C_1$–$C_6$) alkylene group, and $R_{13}$, $R_{14}$ and $R_{15}$ are as defined hereinbefore, $R_{17}$ represents a ($C_3$–$C_6$)cycloalkyl group, $X_5$ represents a group selected from single bond, —CH$_2$—, oxygen atom, sulphur atom optionally substituted by one or two oxygen atoms, and nitrogen atom substituted by hydrogen atom or ($C_1$–$C_6$) alkyl group, $R_{18}$ represents a group selected from:
5- or 6-membered monocycle aryl, heteroaryl, which is optionally substituted by one or more groups, which may be identical or different, selected from ($C_1$-$C_6$)alkyl, halogen, hydroxy, cyano, tetrazolyl, amino, and —C(=O)O$R_7$ wherein $R_7$ represents hydrogen or ($C_1$-$C_6$)alkyl, and 5- or 6-membered monocycle cycloalkyl, heterocycloalkyl, which is optionally substituted by one or more groups, which may be identical or different, selected from ($C_1$-$C_6$)alkyl, halogen, hydroxy, oxo, cyano, tetrazolyl, amino, and —C(=O)O$R_7$ wherein $R_7$ represents hydrogen or ($C_1$-$C_6$)alkyl, m is an integer from 0 to 7 inclusive, the group(s) $R_2$, which may be identical or different independently of each other, is (are) selected from ($C_1$-$C_6$)alkyl, halogen, —CN, $NO_2$, $SCF_3$, —$CF_3$, —$OCF_3$, —$NR_7R_8$, —$OR_8$, —$SR_8$, —$SOR_8$, —$SO_2R_8$, —$(CH_2)_kSO_2NR_7R_8$, -$X_7(CH_2)_kC(=O)OR_8$, —$(CH_2)_kC(=O)OR_8$, -$X_7(CH_2)_kC(=O)NR_7R_8$, —$(CH_2)_kC(=O)NR_7R_8$, and -$X_8$—$R_{20}$ in which:

$X_7$ represents a group selected from oxygen, sulphur optionally substituted by one or two oxygen atoms, and nitrogen substituted by hydrogen or ($C_1$-$C_6$)alkyl, k is an integer from 0 to 3 inclusive, $R_7$ and $R_8$, which may be identical or different independently of each other, are selected from hydrogen and ($C_1$-$C_6$)alkyl, $X_8$ represents a group selected from single bond, —$CH_2$—, oxygen atom, sulphur atom optionally substituted by one or two oxygen atoms, and nitrogen atom substituted by hydrogen atom or ($C_1$-$C_6$)alkyl group, $R_{20}$ represents 5- or 6-membered monocycle aryl, heteroaryl, cycloalkyl, or heterocycloalkyl which is optionally substituted by one or more groups, which may be identical or different, selected from ($C_1$-$C_6$)alkyl, halogen, hydroxy and amino, and when the ring is heterocyclic, it comprises from 1 to 4 heteroatoms selected from nitrogen, oxygen and sulphur, optionally, the racemic forms thereof, isomers thereof, N-oxides thereof, and the pharmaceutically acceptable salts thereof.

According to a first embodiment, the invention relates to compounds of formula (I) wherein:

$G_2$ represents a group selected from C=O, C=S, S(O)$_{n1}$ in which n1 represents an integer from 0 to 2 inclusive, or a group of formula (i/c):

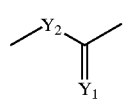

(i/c)

in which the carbon atom with number 1 is attached to the bicycle of the compound of formula (I), $Y_1$ represents a group selected from oxygen, sulphur, —NH and —N($C_1$-$C_6$)alkyl, and $Y_2$ represents a group selected from oxygen, sulphur, —NH and —N($C_1$-$C_6$)alkyl, $X_1$, $X_2$, $X_3$, $G_1$, n, $Z_1$, A, $R_1$, m and $R_2$ are as defined in formula (I).

According to a second embodiment, the invention relates to compounds of formula (I) wherein:

$G_2$ represents a carbon—carbon triple bond, n represents an integer from 1 to 6 inclusive, $X_1$, $X_2$, $X_3$, $G_1$, $Z_1$, A, $R_1$, m and $R_2$ are as defined hereinbefore.

According to a third embodiment, the invention relates to compounds of formula (I) wherein:

$G_2$ represents a carbon—carbon triple bond, n is zero, $Z_1$ is absent,

A represents a group selected from heteroaryl, cycloalkyl, heterocycloalkyl, these groups being 5- or 6-membered monocycle or bicycle composed of two 5- or 6-membered monocycle, $X_1$, $X_2$, $X_3$, $G_1$, $R_1$, m and $R_2$ are as defined hereinbefore.

According to a fourth embodiment, the invention relates to compounds of formula (I) wherein:

$G_2$ represents a carbon—carbon triple bond, n is zero, $Z_1$ is absent,

A represents a phenyl group, $R_1$ represents a hydrogen atom or a group of formula (i/d):

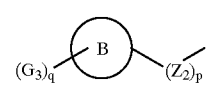

(i/d)

in which p is an integer from 0 to 8 inclusive, $Z_2$ represents —$CR_{11}R_{12}$ wherein $R_{11}$ and $R_{12}$, identical or different independently of each other, represent a group selected from hydrogen, ($C_1$-$C_6$)alkyl, phenyl, trihalogeno($C_1$-$C_6$)alkyl, halogen, amino, $OR_7$, $SR_7$ and —C(=O)O$R_7$ in which $R_7$ represents hydrogen or ($C_1$-$C_6$)alkyl, and wherein when p is greater than or equal to 2, the hydrocarbon chain $Z_2$ optionally contains one or two isolated or conjugated multiple bonds, and/or wherein n is greater than or equal to 2, one of said —$CR_{11}R_{12}$ may optionally be replaced with a group selected from oxygen, S(O)$_{n1}$ in which n1 is as defined hereinbefore, —NH, —N($C_1$-$C_6$)alkyl, and carbonyl, B represents a phenyl group, q is an integer from 1 to 7 inclusive, the group(s) $G_3$, which may be identical or different independently of each other, is (are) selected from —$(CH_2)_kNR_{13}R_{14}$, —$N(R_{13})C(=O)OR_{14}$, —$N(R_{13})SO_2R_{14}$, —$N(SO_2R_{13})_2$, —$S(O)_{k1}R_{13}$, —$SO_2$—$N(R_{13})$—$(CH_2)_{k2}$—$NR_{14}R_{15}$, —$(CH_2)_k$$SO_2NR_{13}R_{14}$, -$X_4(CH_2)_kC(=O)OR_{13}$, —$(CH_2)_kC(=O)OR_{13}$, —C(=O)O—$(CH_2)_{k2}$—$NR_{13}R_{14}$, —C(=O)O—$(CH_2)_{k2}$—C(=O)$OR_{16}$, -$X_4(CH_2)_kC(=O)NR_{13}R_{14}$, —$(CH_2)_kC(=O)NR_{13}R_{14}$, —$R_{17}$—C(=O)$OR_{13}$, -$X_5$—$R_{18}$, —C(=O)—$R_{19}$—$NR_{13}R_{14}$ and -$X_6$—$R_{21}$ in which:

$X_4$ represents a group selected from oxygen atom, sulphur atom optionally substituted by one or two oxygen atoms, and nitrogen atom substituted by a hydrogen atom or a ($C_1$-$C_6$)alkyl group, k is an integer from 0 to 3 inclusive, k1 is an integer from 1 to 2 inclusive, k2 is an integer from 1 to 4 inclusive, $R_{13}$, $R_{14}$ and $R_{15}$, which may be identical or different independently of each other, are selected from hydrogen and ($C_1$-$C_6$)alkyl, $R_{16}$ represents a group selected from ($C_1$-$C_6$)alkyl, —$R_{19}$—$NR_{13}R_{14}$, —$R_{19}$—$NR_{13}$—C(=O)—$R_{19}$—$NR_{14}R_{15}$, and —C(=O)O—$R_{19}$—$NR_{13}R_{14}$ in which $R_{19}$ represents a linear or branched ($C_1$-$C_6$) alkylene group, and $R_{13}$, $R_{14}$ and $R_{15}$ are as defined hereinbefore, R$_{17}$ represents a (C$_3$–C$_6$)cycloalkyl group, X$_5$ represents a group selected from single bond, —CH$_2$—, oxygen atom, sulphur atom optionally substituted by one or two oxygen atoms, and nitrogen atom substituted by hydrogen atom or (C$_1$–C$_6$) alkyl group, R$_{18}$ represents a group selected from heteroaryl, cycloalkyl, heterocycloalkyl, these groups being 5- or 6-membered monocycle or bicycle composed of two 5- or 6-membered monocycle, which is optionally substituted by one or more groups, which may be identical or different independently of each other, selected from (C$_1$–C$_6$)alkyl, halogen, hydroxy, cyano, tetrazolyl, amino, oxo, and —C(=O)OR$_7$ wherein R$_7$ represents hydrogen or (C$_1$–C$_6$)alkyl, X$_6$ represents a group selected from —CH$_2$—, sulphur atom optionally substituted by one or two oxygen atoms, and nitrogen atom substituted by hydrogen atom or (C$_1$–C$_6$)alkyl group, R$_{21}$ represents a phenyl group which is optionally substituted by one or more groups, which may be identical or different independently of each other, selected from (C$_1$–C$_6$)alkyl, halogen, hydroxy, cyano, tetrazolyl, amino, and —C(=O)OR$_7$ wherein R$_7$ represents hydrogen or (C$_1$–C$_6$)alkyl, and X$_1$, X$_2$, X$_3$, G$_1$, m and R$_2$ are as defined in formula (I).

The substituent R$_1$ that is preferred according to the invention is the group of formula (i/d):

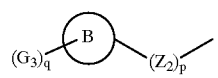

(i/d)

wherein Z$_2$, p, B, G$_3$ and q are as defined in the compound of formula (I).

More particularly, the substituent R$_1$ that is preferred according to the invention is the group of formula (i/d):

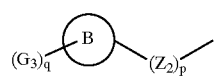

(i/d)

wherein Z$_2$ represents a group —CR$_{11}$R$_{12}$ in which R$_{11}$ and R$_{12}$ represents each a hydrogen atom., and p, B, G$_3$ and q are as defined in the compound of formula (I).

More particularly, the substituent R$_1$ that is preferred according to the invention is the group of formula (i/d):

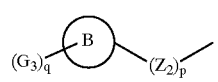

(i/d)

wherein p is one, and Z$_2$, B, G$_3$ and q are as defined in the compound of formula (I).

More particularly, the substituent R$_1$ that is preferred according to the invention is the group of formula (i/d):

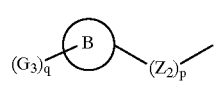

(i/d)

wherein B represents a phenyl group, q is equal to 0 or 1, and G$_3$, when it is present, represents a group selected from OR$_{13}$, halogen, S(O)$_{k1}$R$_{13}$ and (CH$_2$)$_k$C(=O)OR$_{13}$ in which R$_{13}$ represents an hydrogen atom or a (C$_1$–C$_6$)alkyl group, k is zero, and k$_1$ is two, and Z$_2$, p are as defined in the compound of formula (I).

The invention relates also to the compounds of formula (I) wherein G$_1$ represents a group of formula (i/a) in which R$_4$ represents a hydrogen atom or a methyl group, or a group of formula (i/b) in which R$_4$ and R$_5$, identical, represent each a hydrogen atom or a methyl group, and R$_6$ represents a hydrogen atom or a methyl group, and X$_1$, X$_2$, X$_3$, G$_2$, Z$_1$, n, m and R$_2$ are as defined in formula (I).

Preferred compounds of the invention are compounds of formula (I) wherein X$_1$ represents a group —CR$_3$ in which R$_3$ represents a hydrogen atom, X$_2$ represents a nitrogen atom or a group —CR$_3$ in which R$_3$ represents a hydrogen atom, and X$_3$ represents a group —CR$_3$ in which R$_3$ represents a hydrogen atom.

Other preferred compounds of the invention are compounds wherein G$_2$ represents a carbon—carbon triple bond or a group of formula (i/c) in which Y$_1$ represents an oxygen atom, and Y$_2$ represents a group —NH.

Still more preferred compounds of the invention are those compounds of formula (I) wherein Z$_1$ represents —CR$_9$R$_{10}$ in which R$_9$ and R$_{10}$ represent each a hydrogen atom, and n is one.

Especially preferred compounds of the invention are compounds wherein A represents a group selected from phenyl and pyridyl, m is zero or one, and R$_2$ represents a (C$_1$–C$_6$)alkoxy group or a hydrogen atom.

More particularly, the invention relates to the following compounds of formula (I):

3-(4-methoxy-benzyl)-4-oxo-3,4-dihydro-quinazoline-6-carboxylic acid 4-methoxy-benzylamide 3-(4-methoxy-benzyl)-2-methyl-4-oxo-3,4-dihydro-quinazoline-6-carboxylic acid 4-methoxy-benzylamide, hydrochloride 3-(4-methoxy-benzyl)-1-methyl-4-oxo-1,2,3,4-tetrahydro-quinazoline-6-carboxylic acid 4-methoxy-benzylamide 3-(4-methoxy-benzyl)-1,2,2-trimethyl-4-oxo-1,2,3,4-tetrahydro-quinazoline-6-carboxylic acid 4-methoxy-benzylamide 4-[6-(4-methoxy-benzylcarbamoyl)-4-oxo-1,4-dihydro-2H-quinazolin-3-ylmethyl]-benzoic acid 4-[6-(4-methoxy-benzylcarbamoyl)-1-methyl-4-oxo-1,4-dihydro-2H-quinazolin-3-ylmethyl]-benzoic acid methyl ester 4-[6-(4-methoxy-benzylcarbamoyl)-1-methyl-4-oxo-1,4-dihydro-2H-quinazolin-3-ylmethyl]-benzoic acid, 3-(4-fluoro-benzyl)-4-oxo-3,4-dihydro-quinazoline-6-carboxylic acid 3-methoxy-benzylamide 3-(4-methanesulfonyl)-benzyl-4-oxo-3,4-dihydro-quinazoline-6-carboxylic acid 4-methoxy-benzylamide 4-Oxo-3-[4-(pyrrolidine-1-sulfonyl)-benzyl]-3,4-dihydro-quinazoline-6-carboxylic acid 4-methoxy-benzylamide 4-[6-(3-methoxy-benzylcarbamoyl)-4-oxo-4H-quinazolin-3-ylmethyl]-benzoic acid, 3-(4-fluoro-benzyl)-4-oxo-3,4-dihydro-quinazoline-6-carboxylic acid (2-methoxy-pyridin-4-ylmethyl)-amide, 3-(3-fluoro-benzyl)-4-oxo-3,4-dihydro-pyrido[3,4-d]pyrimidine-6-carboxylic acid 3-methoxy-benzylamide, and 3-(3-fluoro-benzyl)-4-oxo-3,4-dihydro-pyrido[3,4-d]pyrimidine-6-carboxylic acid 4-methoxy-benzylamide Further preferred compounds are:
3-(3,4-Difluoro-benzyl)-4-oxo-3,4-dihydro-quinazoline-6-carboxylic acid (2-methoxy-pyridin-4-ylmethyl)-amide
3-(3,4-Difluoro-benzyl)-4-oxo-3,4-dihydro-quinazoline-6-carboxylic acid 4-methoxy-benzylamide.

More particularly, the invention relates also to the following compounds of formula (I):
3-(4-fluorobenzyl)-6-(3-phenyl-prop-1-ynyl)-3H-quinazolin-4-one,
methyl 4-[4-oxo-6-(3-phenyl-prop-1-ynyl)-4H-quinazolin-3-ylmethyl]-benzoate,
4-[4-oxo-6-(3-phenyl-prop-1-ynyl)-4H-quinazolin-3-ylmethyl]-benzoic acid,
3-(4-fluorobenzyl)-6-(3-phenyl-prop-1-ynyl)-3H-pyrido[3,4-d]pyrimidin-4-one,
methyl 4-[6-(3-phenyl-prop-1-ynyl)-4-oxo-4H-pyrido[3,4-d]pyrimidin-3-ylmethyl]-benzoate,
4-[6-(3-phenyl-prop-1-ynyl)-4-oxo-4H-pyrido[3,4-d]pyrimidin-3-ylmethyl]-benzoic acid,
4-[4-oxo-6-(3-phenyl-prop-1-ynyl)-4H-quinazoline-3-ylmethyl]-benzoic acid,
4-{6-[3-(4-methoxy-phenyl)-prop-1-ynyl]-4-oxo-4H-quinazoline-3-ylmethyl}-benzoic acid,
4-[4-oxo-6-(3-phenyl-prop-1-ynyl)-4H-quinazoline-3-ylmethyl]-benzamide
and 3-[(3,5-difluoro-4-hydroxy)-benzyl]-6-(3-phenyl-prop-1-ynyl)-3H-quinazolin-4-one.

Further preferred compounds are:
4-[6-(3-Imidazol-1-yl-prop-1-ynyl)-4-oxo-4H-quinazolin-3-ylmethyl]-benzoic acid
4-[4-Oxo-6-(3-phenyl-prop-1-ynyl)-4H-quinazolin-3-ylmethyl]-benzenesulfonamide
4-[4-Oxo-6-(3-phenyl-prop-1-ynyl)-4H-quinazolin-3-ylmethyl]-benzonitrile
3-(3-Chloro-benzyl)-6-(4-phenyl-but-1-ynyl)-3H-quinazolin-4-one
3-(3-Chloro-benzyl)-6-(3-phenyl-prop-1-ynyl)-3H-quinazolin-4-one
4-[4-Oxo-6-(3-pyrazol-1-yl-prop-1-ynyl)-4H-quinazolin-3-ylmethyl]-benzoic acid
6-(3-Phenyl-prop-1-ynyl)-3-[4-(1H-tetrazol-5-yl)-benzyl]-3H-quinazolin-4-one
3-(3,4-Difluoro-benzyl)-6-[3-(pyridin-4-yloxy)-prop-1-ynyl]-3H-quinazolin-4-one
3-(3,4-Difluoro-benzyl)-6-[3-(4-methoxy-phenyl)-prop-1-ynyl]-3H-quinazolin-4-one
N-{4-[4-Oxo-6-(3-phenyl-prop-1-ynyl)-4H-quinazolin-3-ylmethyl]-phenyl}-acetamide
3-(3,4-Difluoro-benzyl)-6-(3-phenyl-prop-1-ynyl)-3H-quinazolin-4-one
3-(4-Acetyl-benzyl)-6-[3-(4-methoxy-phenyl)-prop-1-ynyl]-3H-quinazolin-4-one
6-(3-Phenyl-prop-1-ynyl)-3-pyridin-4-ylmethyl-3H-quinazolin-4-one
6-[3-(4-Methoxy-phenyl)-prop-1-ynyl]-3-pyridin-4-ylmethyl-3H-quinazolin-4-one Most preferred are the compounds listed in the table below, which refers to the examples later in the application.

Ex. 9
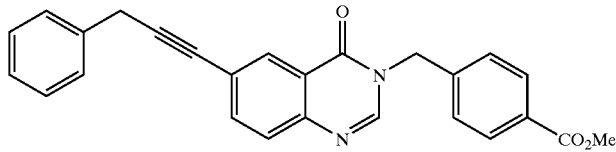
Methyl 4-[4-Oxo-6-(3-Phenyl-prop-1-ynyl)-4H-quinazolin-3-ylmethyl]benzoate Ex. 10, 18
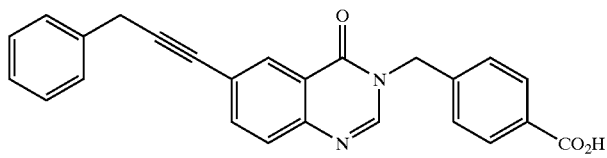
4-[4-Oxo-6-(3-phenyl-prop-1-ynyl)-4H-quinazolin-3-ylmethyl]-benzoic acid Ex. 17
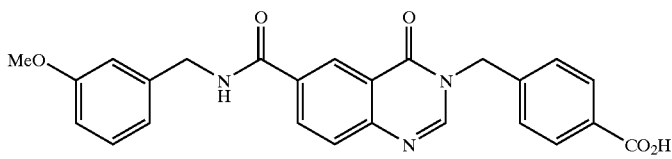
4-[6-(3-Methoxy-benzyl-carbamoyl)-4-oxo-4H-quinazolin-3-ylmethyl] benzoic acid Ex. 19
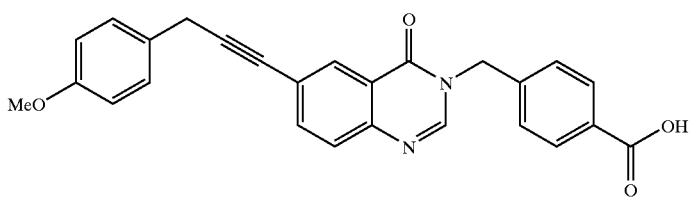
4-{6-[3-(4-Methoxy-phenyl)-prop-1-ynyl]-4-oxo-4H-quinazoline-3-ylmethyl}-benzoic acid -continued

| | | |
|---|---|---|
| Ex. 23 | 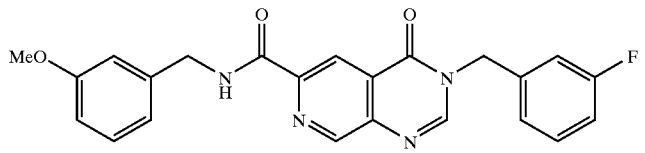 | 3-(3-Fluoro-benzyl)-4-oxo-3,4-di-hydro-pyrido[3,4-d]pyrimi-dine-6 carboxylic acid 3-methoxy-benzylamide |
| Ex. 24 | 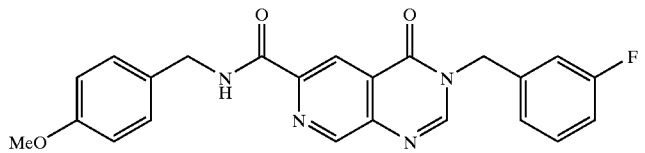 | 3-(3-Fluoro-benzyl)-4-oxo-3,4-di-hydro-pyrido[3,4-d]pyrimi-dine-6 carboxylic acid 4-methoxy-benzylamide |
| Ex. 58 | 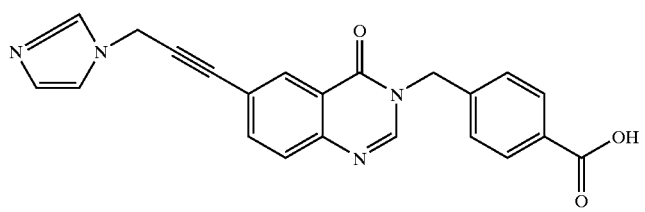 | 4-[6-(3-Imida-zol-1-yl-prop-1-ynyl)-4-oxo-4H-quina-zolin-3-ylmethyl]-benzoic acid |
| Ex. 59 | 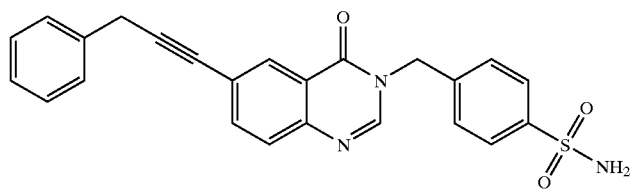 | 4-[4-Oxo-6-(3-phenyl-prop-1-ynyl)-4H-quina-zolin-3-ylmethyl]-benzene-sulfonamide |
| Ex. 60 | 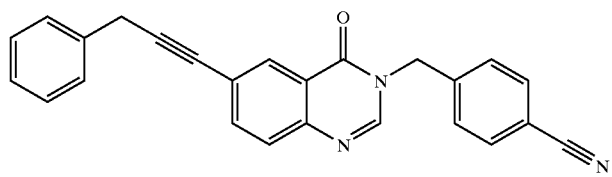 | 4-[4-Oxo-6-(3-phenyl-prop-1-ynyl)-4H-quina-zolin-3-ylmethyl]-benzonitrile |
| Ex. 64 | ClH 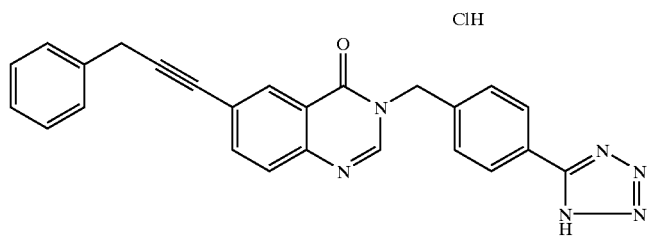 | 6-(3-Phenyl-prop-1-ynyl)-3-[4-(1H-tetra-zol-5-yl)-benzyl]-3H-quina-zolin-4-one |
| Ex. 65 | 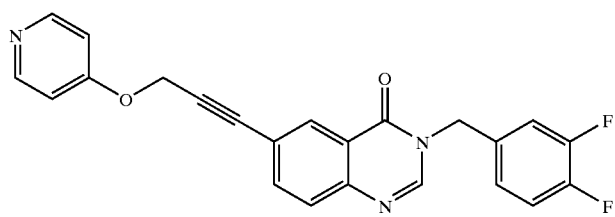 | 3-(3,4-Difluoro-benzyl)-6-[3-(pyri-din-4-yloxy)-prop-1-ynyl]-3H-quina-zolin-4-one |
| Ex. 66 | 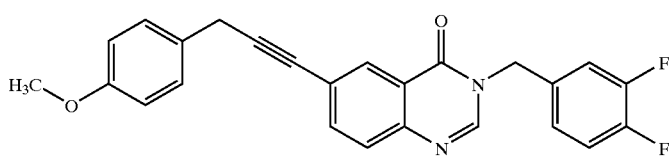 | 3-(3,4-Difluoro-benzyl)-6-[3-(4-meth-oxy-phenyl)-prop-1-ynyl]-3H-quina-zolin-4-one |

-continued

Ex. 67 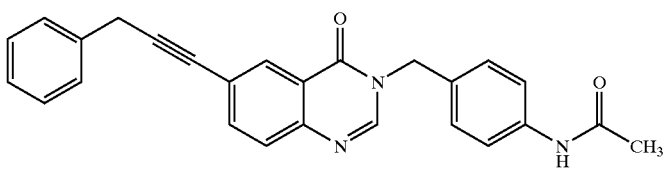 N-{4-[4-Oxo-6-(3-phenyl-prop-1-ynyl)-4H-quinazolin-3-ylmeth-]-phenyl}-acetamide Ex. 69 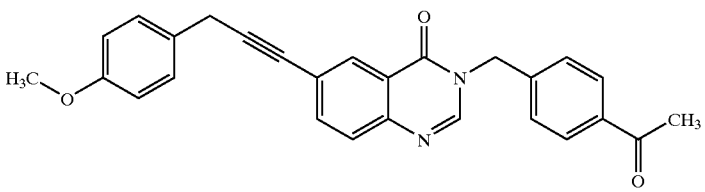 3-(4-Acetyl-benzyl)-6-[3-(4-methoxy-phenyl)-prop-1-ynyl]-3H-quinazolin-4-one Ex. 70 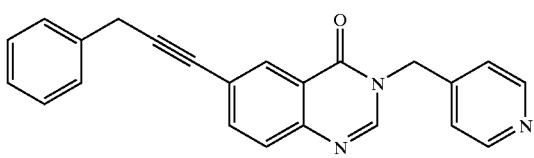 6-(3-Phenyl-prop-1-ynyl)-3-pyridin-4-ylmethyl-3H-quinazolin-4-one Ex. 71 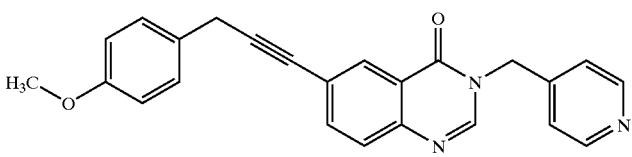 6-[3-(4-Methoxy-phenyl)-prop-1-ynyl]-3-pyridin-4-ylmethyl-3H-quinazolin-4-one The optical isomers, the N-oxides, as well as the addition salts with a pharmaceutically-acceptable acid or base, of the preferred compounds form an integral part of the invention.

The invention also relates to a pharmaceutical composition comprising as active ingredient an effective amount of a compound of formula (I) together with one or more pharmaceutically-acceptable excipients or carriers.

Another embodiment of the invention concerns the use of the compound of formula (I) for the preparation of a medicinal product intended for treating a disease involving therapy by inhibition of matrix metalloprotease, and more particularly of type-13 matrix metalloprotease.

The invention also relates to a method for treating a living body afflicted with a disease involving a therapy by inhibition of matrix metalloprotease, and more particularly of type-13 matrix metalloprotease, the said method comprising the administration of an effective amount of a compound of formula (I) to a patient in need thereof.

A preferred method of treatment according to this invention is treatment of a disease selected from arthritis, rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases, age-related degeneration and cancers.

More particularly, a preferred method of treatment according to this invention is treatment of disease selected from arthritis, osteoarthritis and rheumatoid arthritis.

DETAILED DESCRIPTION OF THE INVENTION

The compounds provided by this invention are those defined in formula (I). In formula (I), it is understood that:

a ($C_1$–$C_6$)alkyl group denotes a linear or branched group containing from 1 to 6 carbon atoms; example of such groups, without implying any limitation are methyl, ethyl, propyl, isopropyl, tert-butyl, neopentyl, hexyl, a ($C_2$–$C_6$)alkenyl group denotes a linear or branched group containing from 2 to 6 carbon atoms, and one or more double bonds; examples of such groups without implying any limitation are vinyl, allyl, 3-buten-1-yl, 2-methyl-buten-1-yl, hexenyl, a ($C_2$–$C_6$)alkynyl group denotes a linear or branched group containing from 2 to 6 carbon atoms, and one or more triple bonds; examples of such groups without implying any limitation are ethynyl, propynyl, 3-butyn-1-yl, 2-methyl-butyn-1-yl, hexynyl, a ($C_1$–$C_6$)alkoxy group means the alkyl group as mentioned above bound through an oxygen atom; examples of such compounds without implying any limitation are methoxy, ethoxy, n-propyloxy, tert-butyloxy, a mono($C_1$–$C_6$)alkylamino denotes a amino group substituted by one ($C_1$–$C_6$)alkyl group as defined hereinbefore; example of such groups, without implying any limitation are methyl amino, isobutyl amino, ethylamino, a di($C_1$–$C_6$)alkylamino denotes a amino group substituted by two ($C_1$–$C_6$)alkyl groups as defined hereinbefore, each alkyl group being identical or different; example of such groups, without implying any limitation are dimethylamino, diethylamino, an aryl group denotes an aromatic monocyclic or bicyclic system containing from 5 to 10 carbon atoms, and in the case of a bicyclic system, one of the ring of which is aromatic in character, and the other ring of which may be aromatic or partially hydrogenated; examples of such groups without implying any limitation are, phenyl, naphthyl, indenyl, benzocyclobutenyl, a heteroaryl group denotes an aryl group as described above in which 1 to 4 carbon atoms are replaced by 1 to 4 hetero atoms selected from oxygen, sulfur and nitrogen; examples of such groups without implying any limitation are furyl, thienyl, pyrrolyl, pyrazolyl, pyridyl, pyrimidyl, pyrazinyl, benzofuryl, benzothienyl, indolyl, quinolyl, isoquinolyl, benzodioxolyl, benzodioxinyl, benzo[1,2,5]thiadiazolyl, benzo[1,2,5]oxadiazolyl, a cycloalkyl group denotes a monocyclic or bicyclic system containing from 3 to 10 carbon atoms, this system being saturated or partially unsaturated but without aromatic character; examples of such groups without implying any limitation are cyclopropyl, cyclobutyl, cyclopentyl, cyclohexyl, cyclooctyl, cycloheptyl, adamantyl, decalinyl, norbornyl, a heterocycloalkyl group denotes a cycloalkyl group as defined hereinbefore in which 1 to 4 carbon atoms are replaced by 1 to 4 hetero atoms selected from oxygen, sulfur, and nitrogen, a bicycle denotes two fused-monocycle and, a trihalogeno($C_1$–$C_6$)alkyl group denotes an alkyl group as defined above which contains a trihalogeno group; examples of such groups without implying any limitation are trifluoromethyl, 2,2,2-trifluoroethyl, a ($C_1$–$C_7$)acyl group denotes an alkyl group or a aryl group as defined above bound through a carbonyl group; examples of such groups without implying any limitation are acetyl, ethylcarbonyl, benzoyl, a multiple bond denotes double bond or triple bond, a halogen atom means fluoro, chloro, bromo or iodo, optical isomers refer to racemates, enantiomers and diastereoisomers.

The invention also relates to the pharmaceutically acceptable salts of the compounds of formula (I). A review of the pharmaceutically acceptable salts will be found in *J. Pharm. Sci.*, 1977, 66, 1–19.

Pharmaceutically acceptable acids mean non-toxic salts derived from mineral or organic acids. Among those there may be mentioned, without implying any limitation, hydrochloric acid, hydrobromic acid, sulfuric acid, phosphonic acid, nitric acid, citric acid, acetic acid, trifluoroacetic acid, lactic acid, pyruvic acid, malonic acid, succinic acid, glutaric acid, fumaric acid, tartaric acid, maleic acid, ascorbic acid, oxalic acid, methanesulfonic acid, camphoric acid, benzoic acid, toluenesulfonic acid, etc. . .

Pharmaceutically acceptable bases mean non-toxic salts derived from mineral or organic bases. Among those, there may be mentioned, without implying any limitation, sodium hydroxide, potassium hydroxide, calcium hydroxide, triethylamine, tert-butylamine, dibenzylethylenediamine, piperidine, pyrrolidine, benzylamine, quaternary ammonium hydroxides etc. . .

A living body is a mammal, including a human, dog, cat, cow, horse, pig, monkey, rat, mouse, sheep, guinea pig, rabbit, and chimpanzee. Preferred living body is a human.

A preferred method of treating cancer is treating breast cancer. More preferred is treating human breast cancer.

The invention also relates to a process for the preparation of compounds of formula (I), which uses as starting material a compound of formula (II):

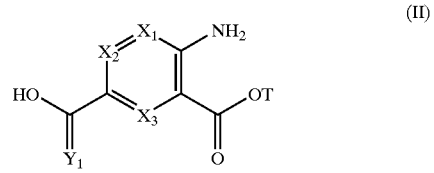

(II)

in which $X_1$, $X_2$, $X_3$, and $Y_1$ have the same definitions as the compound of formula (I), and T represents a group ($C_1$–$C_6$) alkyl, compound of formula (II) which is treated with a compound of formula (III):

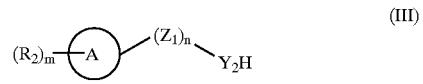

(III)

in which $Z_1$, $Y_2$, $R_2$, A, n and m have the same definitions as the compound of formula (I), by activating the acid function with an activator, in the presence of diisopropylethylamine and a solvent, to yield the compound of formula (IV):

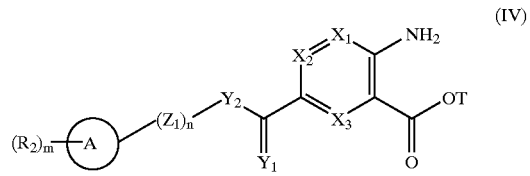

(IV)

in which $X_1$, $X_2$, $X_3$, $Y_1$, T, $Z_1$, $Y_2$, $R_2$, A, n and m are as defined hereinbefore, compound of formula (IV) in which the ester group is hydrolyzed and the subsequently compound obtained is then treated with an activator in the presence of a base and a primary amine with the general formula $R_1$—$NH_2$ in which $R_1$ is as defined in the compound of formula (I), to yield the compound of formula (V):

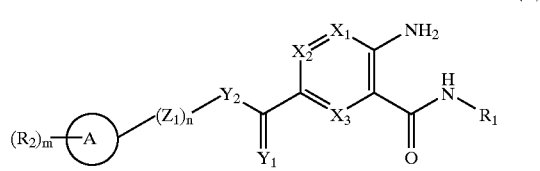

(V)

in which $X_1$, $X_2$, $X_3$, $Y_1$, $Y_2$, $Z_1$, $R_2$, $R_1$, A, n and m are as defined hereinbefore, which compound of formula (V) is treated:
either with triethyl orthoformate under heating condition, to yield the compound of formula (I/a), which is a particular case of the compound of formula (I):

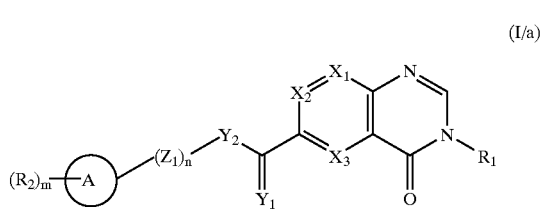

(I/a)

in which $X_1$, $X_2$, $X_3$, $Y_1$, $Y_2$, $Z_1$, $R_2$, $R_1$, A, n and m are as defined hereinbefore,
or under heating condition in the presence of acid, with a compound of formula (VI):

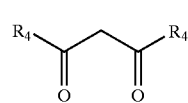

(VI)

in which $R_4$ has the same definition as the compound of formula (I), to yield the compound of formula (I/b), which is a particular case of the compound of formula (I):

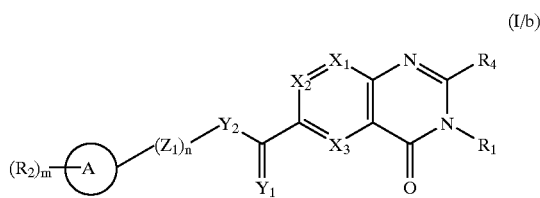

(I/b)

in which $X_1$, $X_2$, $X_3$, $Y_1$, $Y_2$, $Z_1$, $R_2$, $R_1$, $R_4$, A, n and m are as defined hereinbefore,
or with a compound of formula (VII) in basic condition:

(VII)

in which $R_4$ and $R_5$ have the same definition as the compound of formula (I),
to yield the compound of formula (I/c), which is a particular case of the compound of formula (I):

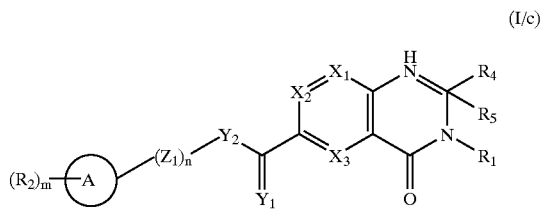

(I/c)

in which $X_1$, $X_2$, $X_3$, $Y_1$, $Y_2$, $Z_1$, $R_2$, $R_1$, $R_4$, $R_5$, A, n and m are as defined hereinbefore,
which compound of formula (I/c) is optionally treated with a hydride, in the presence of a compound of formula (VIII):

$R_6$-Hal (VIII)

in which $R_6$ has the same definition as the compound of formula (I),
to yield the compound of formula (I/d), which is a particular case of the compound of formula (I):

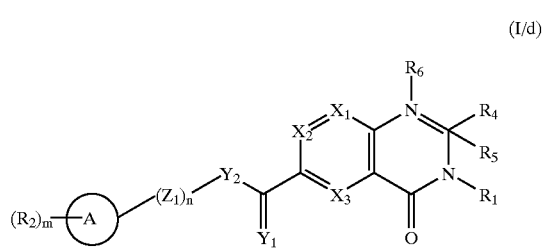

(I/d)

in which $X_1$, $X_2$, $X_3$, $Y_1$, $Y_2$, $Z_1$, $R_2$, $R_1$, $R_4$, $R_5$, $R_6$, A, n and m are as defined hereinbefore,
compounds of formulae (I/a), (I/b), (I/c) and (I/d) constitute some compounds of the invention, which are purified, where appropriate, according to a conventional purification technique, which are separated, where appropriate, into their different isomers according to a conventional separation technique, and which are converted, where appropriate, into addition salts thereof with a pharmaceutically-acceptable acid or base, or into N-oxide thereof.

The invention also relates to a process for the preparation of compounds of formula (I), which uses as starting material a compound of formula (X):

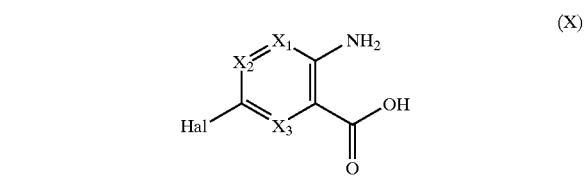

(X)

in which $X_1$, $X_2$, and $X_3$ have the same definitions as the compound of formula (I), and Hal represents a halogen atom,
which compound of formula (X) is treated in a first step with a derivate of phosgene to yield the compound of formula (XI):

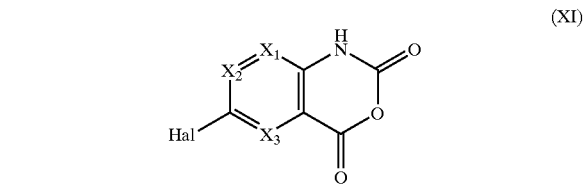

(XI)

in which $X_1$, $X_2$, $X_3$ and Hal are as defined hereinbefore, which compound of formula (XI) is treated in basic medium with a primary amine of general formula $R_1$—$NH_2$ in which $R_1$ has the same definition as in the compound of formula (I), to yield the compound of formula (XII):

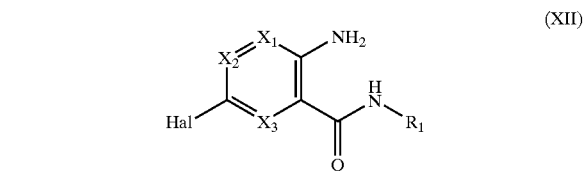

(XII)

in which $X_1$, $X_2$, $X_3$, $R_1$ and Hal are as defined hereinbefore, which compound of formula (XII) is treated:
either with triethyl orthoformate under heating condition, to yield the compound of formula (XIII/a):

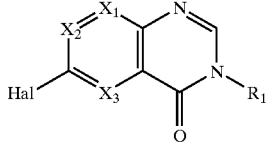

(XIII/a)

in which $X_1$, $X_2$, $X_3$, $R_1$ and Hal are as defined hereinbefore,
or under heating condition in the presence of an acid, with a compound of formula (VI):

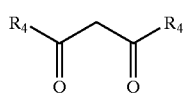

(VI)

in which $R_4$ has the same definition as the compound of formula (I), to yield the compound of formula (XIII/b):

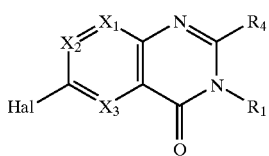

(XIII/b)

in which $X_1$, $X_2$, $X_3$, Hal, $R_1$ and $R_4$ are as defined hereinbefore,
or with a compound of formula (VII) in basic conditions:

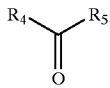

(VII)

in which $R_4$ and $R_5$ have the same definition as the compound of formula (I),
to yield the compound of formula (XIII/c):

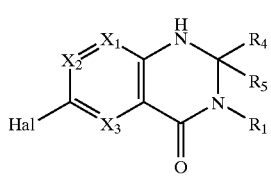

(XIII/c)

in which $X_1$, $X_2$, $X_3$, Hal, $R_1$, $R_4$ and $R_5$ are as defined hereinbefore,
which compound of formula (XIII/c) is optionally treated with a hydride, in the presence of a compound of formula (VIII):

 $R_6$-Hal  (VIII)

in which $R_6$ has the same definition as the compound of formula (I), and Hal is a halogen atom, to yield the compound of formula (XIII/d), which is a particular case of the compound of formula (I):

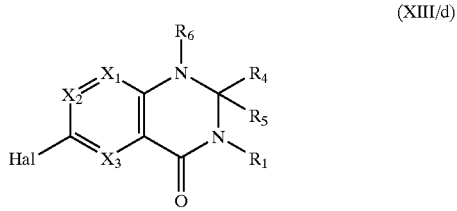

(XIII/d)

in which $X_1$, $X_2$, $X_3$, Hal, $R_1$, $R_4$, $R_5$ and $R_6$ are as defined hereinbefore, all compounds of formulae (XIII/a), (XIII/b), (XIII/c) and (XIII/d) constitute the compound of formula (XIII/e):

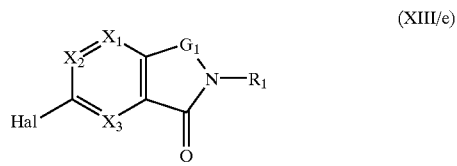

(XIII/e)

in which $X_1$, $X_2$, $X_3$, Hal, $R_1$ and $G_1$ are as defined in the compound of formula (I), compound of formula (XIII/e) which is treated under conditions of palladium-catalyzed alkynylation with a compound of formula (XIV):

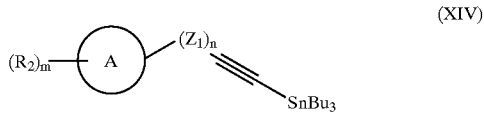

(XIV)

in which $Z_1$, $R_2$, A, n and m have the same definitions as the compound of formula (I), to yield the compound of formula (I/e), which is a particular case of the compound of formula (I):

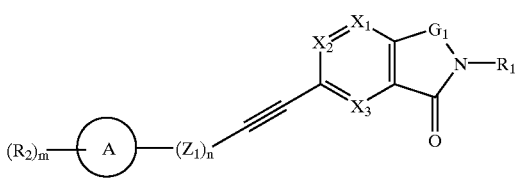

(I/e)

in which $X_1$, $X_2$, $X_3$, $R_1$, $G_1$, $Z_1$, $R_2$, A, n and m have the same definitions as the compound of formula (I), compounds of formula (I/e) constitute some compounds of the invention, which are purified, where appropriate, according to a conventional purification technique, which are separated, where appropriate, into their different isomers according to a conventional separation technique, and which are converted, where appropriate, into addition salts thereof with a pharmaceutically-acceptable acid or base, or into N-oxide thereof.

An alternative way to obtain the compound of formula (XIII/a) from compound of formula (XI) is described in the following scheme 1:

Scheme 1

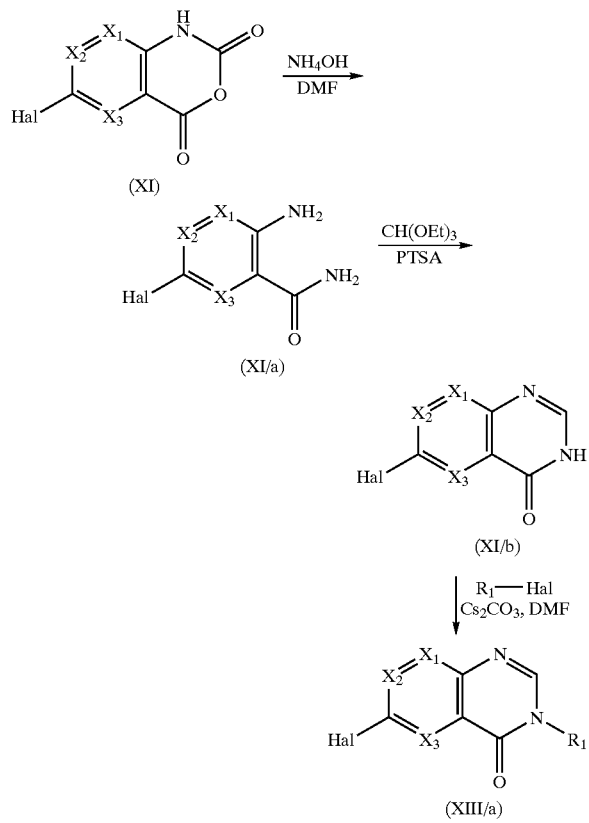

Wherein $X_1$, $X_2$, $X_3$, $R_1$ and Hal, are as defined above.

In a first step, compound of formula (XI) is treated with an aqueous solution of ammonium hydroxide to yield compound of formula (XI/a) which is reacted with triethyl orthoformate in the presence of a catalytic amount of acid like para-toluene sulfonic acid (PTSA). The 3H-quinazolin-4-one (XI/b) obtained is condensed in basic medium to a compound of formula $R_1$-Hal, in which $R_1$ is as defined in the compound of formula (I) and Hal represents a halogen, to yield the compound of formula (XIII/a).

The invention also relates to a process for the preparation of compounds of formula (I), which uses as starting material a compound of formula (XIII/e):

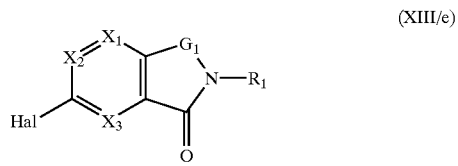

in which $X_1$, $X_2$, $X_3$, $R_1$ and $G_1$ are as defined in the compound of formula (I), and Hal is a halogen atom, compound of formula (XIII/e) which is condensed, in the presence of dichlorobis(triphenylphosphine)palladium, cupper iodide and N,N'-diisopropylethylamine in dimethylformamide, on a compound of formula (XV):

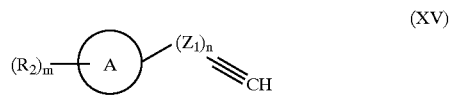

in which $Z_1$, $R_2$, A, n and m have the same definitions as the compound of formula (I), to yield the compound of formula (I/e), which is a particular case of the compound of formula (I):

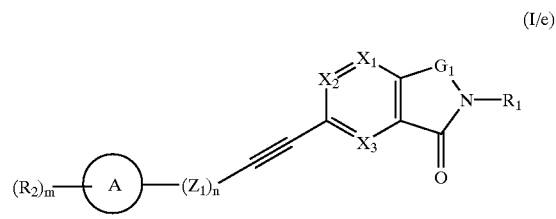

in which $X_1$, $X_2$, $X_3$, $R_1$, $G_1$, $Z_1$, $R_2$, A, n and m have the same definitions as the compound of formula (I).

The invention also relates to a process for the preparation of compounds of formula (I), which uses as starting material a compound of formula (XIII/e):

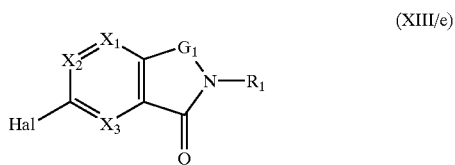

in which $X_1$, $X_2$, $X_3$, $R_1$ and $G_1$ are as defined in the compound of formula (I), and Hal, is a halogen atom, compound of formula (XIII/e) which is reacted with carbon monoxide in an alkaline medium in the presence of a protic solvent like methanol and a catalytic amount of palladium, to yield the compound of formula (XVI):

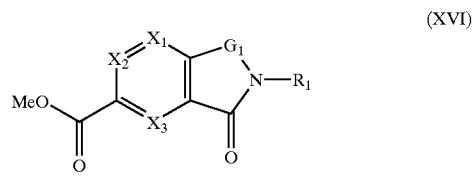

in which $X_1$, $X_2$, $X_3$, $R_1$ and $G_1$ are as defined in the compound of formula (I),
compound of formula (XVI) which is hydrolysed under basic medium to yield the compound of formula (XVII):

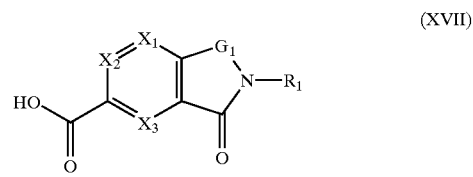

in which $X_1$, $X_2$, $X_3$, $R_1$ and $G_1$ are as defined in the compound of formula (I), compound of formula (XVII) which is condensed under basic medium in the presence of a Mukayama reagent, on the compound of formula (XVIII):

(XVIII)

in which $Z_1$, $R_2$, A, n and m have the same definitions as the compound of formula (I), to yield the compound of formula (I/f), which is a particular case of the compound of formula (I):

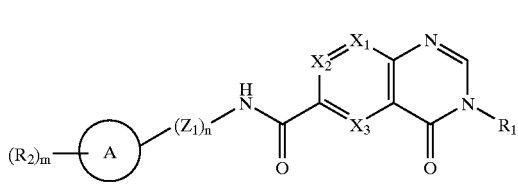

(I/f)

in which $X_1$, $X_2$, $X_3$, $Z_1$, $R_2$, $R_1$, A, n and m are as defined hereinbefore, compounds of formula (I/f) constitute some compounds of the invention, which are purified, where appropriate, according to a conventional purification technique, which are separated, where appropriate, into their different isomers according to a conventional separation technique, and which are converted, where appropriate, into addition salts thereof with a pharmaceutically-acceptable acid or base, or into N-oxide thereof.

The invention also relates to a process for the preparation of compounds of formula (I), which uses as starting material a compound of formula (XIX):

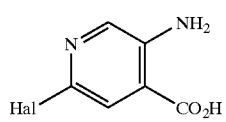

(XIX)

in which Hal represents a halogen atom, compound of formula (XIX) which is heated in the presence of formamidine acetate in a polar solvent like 2-methoxyethan-1-ol, to yield the compound of formula (XX):

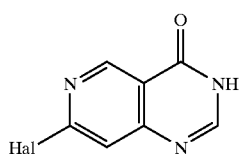

(XX)

in which Hal is as defined hereinbefore, compound of formula (XX) which is treated in basic medium with a compound of formula $R_1$-Hal, in which $R_1$ is as defined in the compound of formula (I) and Hal represents a halogen atom, to yield the compound of formula (XXI):

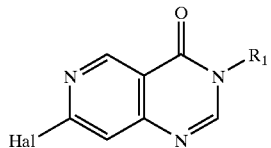

(XXI)

in which Hal and $R_1$ are as defined hereinbefore, compound of formula (XXI) which is reacted with carbon monoxide under basic medium in the presence of an alcoholic solvent like methanol and a catalytic amount of palladium like $PdCl_2$(dppf), to yield the compound of formula (XXII):

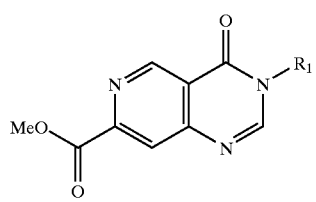

(XXII)

in which $R_1$ is as defined hereinbefore, compound of formula (XXII) which is condensed, in the presence of trimethylaluminium, with a compound of formula (XVIII):

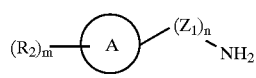

(XVIII)

in which $Z_1$, $R_2$, A, n and mn have the same definitions as the compound of formula (I), to yield the compound of formula (I/g), which is a particular case of the compound of formula (I):

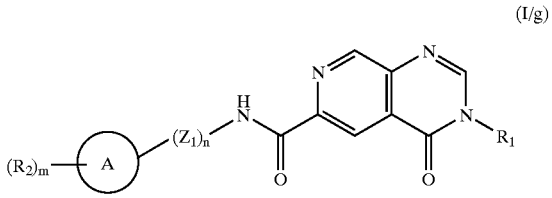

(I/g)

in which $Z_1$, $R_2$, $R_1$, A, n and m are as defined hereinbefore, compounds of formula (I/g) constitute some compounds of the invention, which are purified, where appropriate, according to a conventional purification technique, which are separated, where appropriate, into their different isomers according to a conventional separation technique, and which are converted, where appropriate, into addition salts thereof with a pharmaceutically-acceptable acid or base, or into N-oxide thereof.

The compounds of the invention that are present in the form of a mixture of diastereoisomers are isolated in a pure form by using conventional separation techniques such as chromatography.

As mentioned above, compounds of formula (I) of the present invention are matrix metalloprotease inhibitors, and more particularly inhibitors of the enzyme MMP-13.

In this respect, their use is recommended for the treatment of diseases or complaints involving a therapy by MMP-13 inhibition. By way of example, the use of the compounds of the present invention may be recommended for the treatment of any pathology in which destruction of extracellular matrix tissue occurs, and most particularly pathologies such as arthritis, rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary disease, age-related macular degeneration and cancers.

The present invention also relates to pharmaceutical compositions comprising as active ingredient at least one compound of formula (I), an isomer thereof, a N-oxide thereof, or an addition salt thereof with a pharmaceutically-acceptable acid or base, alone or in combination with one or more pharmaceutically-acceptable, inert, non-toxic excipients or carriers.

Among the pharmaceutical compositions according to the invention, there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

Pharmaceutical compositions according to the invention for parenteral injections especially include aqueous and non-aqueous sterile solutions, dispersions, suspension and emulsions, and also sterile powders for reconstituting injectable solutions or dispersions.

Pharmaceutical compositions according to the invention for oral administration in solid form especially include tablets or dragees, sublingual tablets, sachets, gelatin capsules and granules, for oral, nasal, buccal or ocular administration in liquid form, especially include emulsions, solutions, suspensions, drop, syrups and aerosols.

Pharmaceutical compositions for rectal or vaginal administration are preferably suppositories, and those for per- or trans-cutaneous administration especially include powders, aerosols, creams, ointment, gels and patches.

The pharmaceutical compositions mentioned hereinbefore illustrate the invention but do not limit it in any way.

Among the pharmaceutically acceptable, inert, non-toxic excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colourants, aromatizing agents etc...

The useful dosage varies according to the age and weight of the patient, the administration route, the pharmaceutical composition used, the nature and severity of the disorder and the administration of any associated treatments. The dosage ranges from 2 mg to 1 g per day in one or more administrations. The compositions are prepared by methods that are common to those skilled in the art and generally comprise 0.5% to 60% by weight of active principle (compound of formula (I)) and 40% to 99.5% by weight of pharmaceutically acceptable excipients or carriers.

The examples that follow illustrate the invention but do not limit it in any way.

The starting materials used are products that are known or that are prepared according to known operating procedures. The various preparations yield synthetic intermediates that are useful in preparation of the compounds of the invention. Some of these intermediates are new compounds.

The structures of the compounds described in the Examples and Preparations were determined according to the usual spectrophotometric techniques (infrared, nuclear magnetic resonance, mass spectrometry, . . . )

In the Preparations and Examples, it is understood that:

DMF means Dimethylformamide,

THF means tetrahydrofurane,

DMSO means dimethylsulfoxide,

TOTU means O-(ethoxycarbonyl)cyanomethylamino]-N-N-N'-N'-tetramethyl uronium fluoroborate, DIPEA means diisopropylethylamine.

EXAMPLES

Preparation 1: 4-Amino-3-[(4-methoxy)-benzylcarbamoyl]1-carboxylic acid 4-methoxy-benzylamide Step 1: 4-Amino-isophthalic acid 6.3 g (150 mmol) of LiOH.H$_2$O are added to a stirred solution of 15.7 g (75 mmol) of methyl 4-amino-isophtalate in 300 ml of dioxane and 1200 ml of water. The reaction mixture is heated for 1 hour to 100° C., cooled and acidified to pH=1 by the addition of concentrated HCl. A precipitate is obtained then filtered off, washed, and dried under vacuum to yield 13 g (yield=95.7%) of the desired compound.

N.M.R (DMSO-d$_6$) $^1$H δ (ppm): 6.80 (d, 1H); 6.80–7.80 (bs); 7.80 (dd, 1H); 8.35 (s, 1H); 11.9–13.1 (bs).

Step 2: 4-Amino-3-[(4-methoxy)-benzylcarbamoyl]-phenyl-1-carboxylic acid 4-methoxy-benzylamide

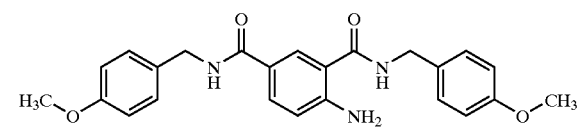

2.25 g (16.5 mmol) of 4-methoxybenzylamine, 5.4 g (16.5 mmol) of TOTU and 5.4 ml (3.9 g, 30 mmol) of DIPEA are added successively to a stirred solution of 2.7 g (15 mmol) of the compound obtained in Step 1 to 100 ml of DMF. The reaction mixture is stirred overnight at room temperature, then the solvent is removed under vacuum. The crude mixture is taken up in dichloromethane, and washed successively with HCl 1N and NaOH 1N. After separation by decantation the organic phase is dried over Na$_2$SO$_4$ and concentrated under vacuum. The crude product is purified by chromatography and concretized from a mixture of dichloromethane and ether to yield 3.1 g (yield=49.3%) of the desired compound.

N.M.R (DMSO-d$_6$) $^1$H δ (ppm): 3.70 (s, 6H); 4.35 (t, 4H); 6.70 (d, 1H); 6.80–6.90 (m, 6H); 7.20–7.30 (m, 4H); 7.65 (dd, 1H); 8.10 (s, 1H); 8.45 (t,1H); 8.75 (t, 1H).

Preparation 2: Methyl 4-{[2-Amino-5-(4-methoxy-benzylcarbamoyl)-benzoylamino]-methyl}-benzoate Step 1: Methyl 6-Amino-N-(4-methoxy-benzyl)-isophthalate

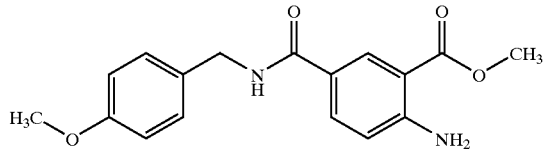

6.56 g (20 mmol) of TOTU and 2.6 ml (2.74 g, 20 mmol) of 4-methoxybenzylamine are added to a stirred solution of 4.2 g (18.1 mmol) of 4-amino-3-methylcarboxylate-1-phenyl carboxylic acid in 150 ml of anhydrous DMF. The mixture is cooled at 0° C. and 9.5 ml (7.02 g, 54.3 mmol) of DIPEA are added. The reaction mixture is stirred overnight at room temperature and concentrated under vacuum. The residue is taken up in 150 ml of dichloromethane, washed with 100 ml of a saturated solution of $NaHCO_3$. The organic layer is dried and concentrated under vacuum. After a chromatography over silica gel 3.5 g (yield=62%) of the desired compound are isolated.

TLC: $CH_2Cl_2$/MeOH 90/10 Rf=0.80.

N.M.R (DMSO-$d_6$) $^1$H δ (ppm): 3.80 (s, 3H); 3.90 (s, 3H); 4.55 (d, 2H); 6.0–6.15 (bs, 2H); 6.15–6.30 (bs, 1H); 6.65 (d, 1H); 6.90 (d, 1H); 7.25–7.30 (m, 2H); 7.80 (d, 1H); 8.25 (s, 1H).

PURITY: HPLC=98.5%

Step 2: 6-Amino-N-(4-methoxy-benzyl)-isophthalamic acid

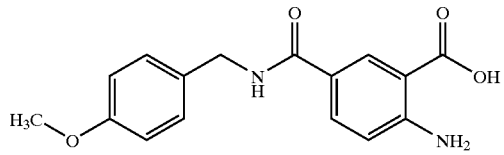

0.3 g (7 mmol) of LIOH, $H_2O$ is added to a stirred solution of 1.1 g (3.5 mmol) of the compound obtained in the preceding Step 2 in 10 ml of dioxane and 40 ml of water. The reaction mixture is heated under reflux for 2 hours, cooled, and acidified at pH=1 by addition of concentrated HCl. The precipitate obtained is filtered off and dried to give the desired compound.

N.M.R (DMSO-$d_6$) $^1$H δ (ppm): 3.70 (s, 3H); 4.35 (d, 2H); 6.75 (d, 1H); 6.85 (d, 2H); 7.20 (d, 2H); 7.75 (dd, 1H); 8.30 (s 1H); 8.65 (t, 1H).

Step 3: Methyl 4-{[2-Amino-5-(4-methoxy-benzylcarbamoyl)-benzoylamino]-methyl}-benzoate

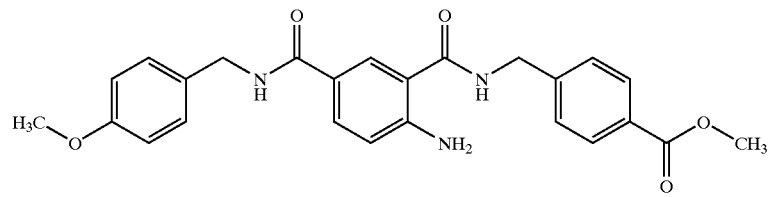

The desired compound is obtained according to the procedure described in the Step 1 of Preparation 2 using as starting material the compound obtained in the preceding step 2 and as reactant the methyl 4-(aminomethyl)benzoate hydrochloride. It is purified by chromatography over silica gel using a mixture of dichloromethane/ether as eluant.

N.M.R (DMSO-$d_6$) $^1$H δ (ppm): 3.70 (s, 3H); 3.85 (s, 3H); 4.40 (d, 2H); 4.50 (d, 2H); 6.70 (d, 1H); 6.80–6.90 (m, 4H); 7.25 (d, 2H); 7.45 (d, 2H); 7.70 (dd, 1H); 7.95 (d, 2H); 8.15 (s, 1H); 8.45 (t, 1H); 8.90 (t, 1H).

Preparation 3: 3-(4-fluorobenzyl)-6-iodo-3H-quinazolin-4-one

Step 1: 6-iodo-1H-benzo[a][1,3]oxazine-2,4-dione

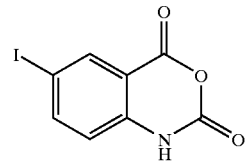

To a suspension of 2-amino-5-iodobenzoic acid (4.9 g, 18.0 mmol) in $H_2O$ (20 ml) and concentrated HCl (5 ml) is added dioxane (50 ml) until a clear solution is obtained. Neat diphosgene (5.95 g, 30.0 mmol) is added dropwise (with cooling at times so that the solution would not boil) to give a white precipitate. After stirring at room temperature for 10 min., $H_2O$ (ca. 100 ml) is added and the precipitate is filtered and washed with copious amount of $H_2O$. It is dried in vacuo to give the desired product (5.2 g, quantitative) as white crystals.

N.M.R (DMSO-$d_6$) $^1$H δ (ppm): 6.93 (d, J=8.6 Hz, 1H), 8.00 (dd, J=8.6, 2.0 Hz, 1H), 8.10 (d, J=2.0 Hz, 1H), 11.8 (s, 1H);

MS (APCI), M/z 288.0 (M−1).

Step 2: 2-amino-N-(4-fluorobenzyl)-5-iodo-benzamide

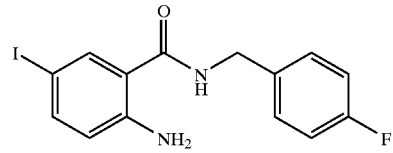

To a 50° C. solution of the compound obtained in the preceding Step 1(2.1 g, 7.27 mmol) in DMF (20 ml) are added neat 4-fluorobenzylamine (1.18 g, 9.45 mmol) dropwise. The reaction is stirred at room temperature for 10 min. while bubbling is observed ($CO_2$), and TLC indicated the completion of the reaction. The reaction content is poured into a separatory funnel charged with $CH_2Cl_2$ and $H_2O$. After separation, the organic layer is washed with $H_2O$(3×50 ml) and brine (50 ml). It is dried ($Na_2SO_4$), filtered and concentrated in vacuo to give a white solid which is purified using flash chromatography to give the desired compound as a white solid (2.5 g, 93%).

N.M.R (DMSO-$d_6$) $^1$H δ (ppm): 5.15 (d, J=5.8 Hz, 2H), 6.50 (s, 1H), 7.03 (m, 1H); 7.34 (m, 1H), 7.43 (d, J=8.5 Hz, 1H), 8.02 (m, 1H), 8.10 (s, 1H), 8.66 (d, j=1.9 Hz, 1H), 9.18 (t, J=5.8 Hz, 1H);

MS (APCI), M/z 371.0 (M+1).

Step 3: 3-(4-fluorobenzyl)-6-iodo-3H-quinazolin-4-one

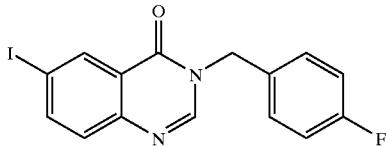

To the solution of the compound obtained in the preceding Step 2 (2.69 g, 7.27 mmol) in triethyl orthoformate is added catalytic amount of TsOH. The solution is refluxed for 5 h, cooled to room temperature. After removal of all volatiles in vacuo, the residue is purified using flash chromatography to give the desired quinazolinone as a brownish solid. Trituration then afforded the desired compound as a white solid (1.56 g, 58%).

N.M.R (DMSO-$d_6$) $^1$H δ (ppm): 5.15 (s, 2H), 7.03 (m, 1H); 7.34 (m, 1H), 7.43 (d, J=8.5 Hz, 1H), 8.02 (m, 1H), 8.10 (s, 1H), 8.66 (d, J=1.9 Hz, 1H);

MS (APCI), M/z 381.0 (M+1).

Preparation 4: Methyl 4-(6-Iodo-4-oxo-4H-quinazolin-3-ylmethyl)-benzoate

Step 1: Methyl 4-[(2-Amino-5-iodo-benzoylamino)-methyl]-benzoate

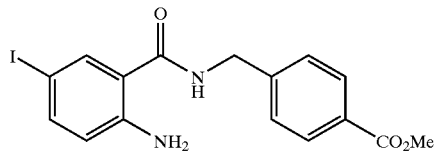

To a 50° C. solution of the compound obtained in the Step 1 of Preparation 3 (1.4 g, 4.84 mmol) in DMF (20 ml) is added the hydrochloride salt of 4-carbomethoxy-benzylamine (1.17 g, 5.8 mmol). The reaction is stirred at room temperature for 1 h while bubbling is observed ($CO_2$), and TLC indicated the completion of the reaction. The reaction content is poured into a separatory funnel charged with $CH_2Cl_2$ and $H_2O$. After separation, the organic layer is washed with $H_2O$ three times to remove DMF. It is then washed with brine, dried ($Na_2SO_4$), filtered and concentrated in vacuo to give the desired amide as a brown solid (2.0 g, quantitative).

N.M.R (DMSO-$d_6$) $^1$H δ (ppm): 3.31 (s, 3H), 4.36 (d, J=5.9 Hz, 2H), 6.55 (d, J=8.6 Hz, 1H), 6.59 (s, 2H), 7.15 (m, 2H), 7.35 (m, 4H), 7.80 (d, J=1.9 Hz, 1H), 8.88 (t, J=5.9 Hz, 1H);

MS (APCI), M/z 411.0 (M+1).

Step 2: Methyl 4-(6-Iodo-4-oxo-4H-quinazolin-3-ylmethyl)-benzoate

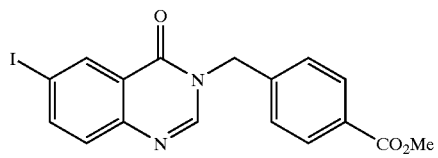

To a solution of the compound obtained in the preceding Step 1 (2.0 g, 4.84 mmol) in triethyl orthoformate is added catalytic amount of TsOH. The solution is refluxed for 5 h, cooled to room temperature. After removal of all volatile solvents in vacuo, the residue is purified using flash chromatography to give the desired quinazolinone as a brownish solid. Trituration then afforded the desired compound as a white solid (1.0 g, 50%).

N.M.R (CDCl$_3$) $^1$H δ (ppm) 3.31 (s, 3H), 5.26 (d, 2H), 7.48 (m, 4 H), 7.90 (d, J=6.8 Hz, 2H), 8.10 (m, 1H), 8.40 (d, J=1.7 Hz, 1H), 8.60 (d, J=1.5 Hz, 1H);

MS (APCI), M/z 421.3 (M+1).

Preparation 5: 3-(4-Fluoro-benzyl)-6-iodo-3H-pyrido[3,4-d]pyrimidin-4-one

Step 1: 6-Iodo-1H-pyrido[3,4-d][1,3]oxazine-2,4-dione

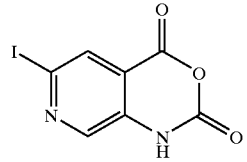

To a suspension of 2-amino-5-iodo-isonicotinic acid (18.0 mmol) in $H_2O$ (20 ml) and concentrated HCl (5 ml) is added dioxane (50 ml) until a clear solution is obtained. Neat diphosgene (5.95 g, 30.0 mmol) is added dropwise (with cooling at times so that the solution does not boil) until a precipitate formed. After stirring at room temperature for 10 minutes, $H_2O$ (100 ml) is added, and the precipitate is filtered and washed with a copious amount of $H_2O$. The filter cake is dried in vacuo to give the desired compound.

Step 2: 5-Amino-N-(4-fluoro-benzyl)-2-iodo-isonicotinamide

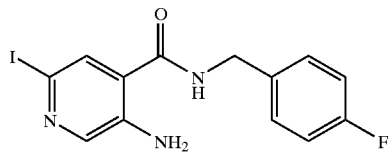

To a 50° C. solution of a compound obtained in Step 1 (7.27 mmol) in DMF (20 ml) is added 4-fluorobenzylamine (9.45 mmol) dropwise. The reaction is stirred at room temperature for 10 minutes while bubbling is observed ($CO_2$), and TLC indicates completion of the reaction. The reaction content is poured into a separatory funnel charged with $CH_2Cl_2$ and $H_2O$. After separation, the organic layer is washed with $H_2O$ (3×50 ml) and brine (50 ml). The organic layers are then dried ($Na_2SO_4$), filtered and concentrated in vacuo, and the residue optionally is purified using flash chromatography on silica gel to give the desired compound.

Step 3: 3-(4-Fluoro-benzyl)-6-iodo-3H-pyrido[3,4-d]pyrimidin-4-one

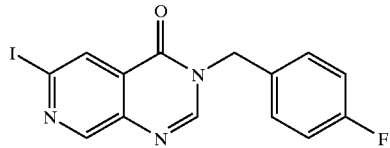

To a solution of the compound obtained in Step 2 (7.27 mmol) in triethyl orthoformate is added a catalytic amount of para-toluenesulfonic acid. The solution is refluxed for 5 hours, and cooled to room temperature. After removal of all volatiles in vacuo, the residue is purified using flash chromatography on silica gel to give the desired compound.

Preparation 6: Methyl 4-(6-Iodo-4-oxo-4H-pyrido [3,4-d]pyrimidin-3-ylmethyl)-benzoate Step 1: Methyl 4-{[(5-Amino-2-iodo-pyridine-4-carbonyl)-amino]-methyl}-benzoate

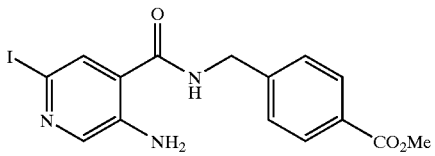

To a 50° C. solution of the compound obtained in the Step 1 of Preparation 6 (4.84 mmol), in DMF (20 ml) is added the hydrochloride salt of 4-carbomethoxy-benzylamine (1.17 g, 5.8 mmol). The reaction is stirred at room temperature for 1 hour while bubbling is observed ($CO_2$ evolution), and TLC indicates the completion of the reaction. The reaction content is poured into a separatory funnel charged with $CH_2Cl_2$ and $H_2O$. After separation of the layers, the organic layer is washed with $H_2O$ three times to remove DMF. The organic layer is then washed with brine, dried ($Na_2SO_4$), filtered, and concentrated in vacuo to give the desired compound.

Step 2: Methyl 4-(6-Iodo-4-oxo-4H-pyrido[3,4-d]pyrimidin-3-ylmethyl)-benzoate

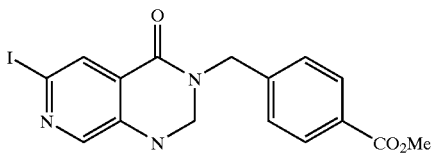

To a solution of the compound obtained in Step 1 (4.84 mmol) in triethyl orthoformate is added a catalytic amount of TsOH. The solution is refluxed for 5 hours, and cooled to room temperature. After removal of all volatile solvents in vacuo, the residue is purified using flash chromatography on silica gel to give the desired compound.

Preparation 7: 3-(4-Fluoro-benzyl)-4-oxo-3,4-dihydro-quinazoline-6-carboxylic acid Step 1: Methyl 3-(4-fluoro-benzyl)-4-oxo-3,4-dihydro-quinazoline-6-carboxylate

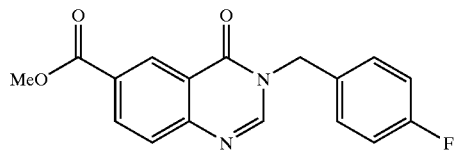

2.0 g (5.27 mmol) of the compound prepared from preparation 3, is dissolved in 50 ml of 1:1 DMF:Methanol, an excess amount of triethylamine, and a catalytic amount of Pd(dppf)$Cl_2$. The reaction solution is poured into an autoclave and heated at 100° C. for 4 hours under carbon monoxide atmosphere. The reaction is cooled to room temperature and filtered. The filtrate is concentrated in vacuo and the residue purified on a silica gel column using 1:1 Hex:EtOAc to yield the desired product as a white solid (100%).

Step 2: 3-(4-Fluoro-benzyl)-4-oxo-3,4-dihydro-quinazoline-6-carboxylic acid

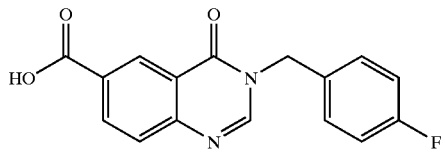

1.7 g (5.27 mmol) of the compound obtained in the preceding Step 1 is dissolved in 50 ml of 90% THF:10% Water. 10 equivalents of LiOH is added, and the reaction solution is refluxed for 5 hours. The reaction solution is diluted with 100 ml of water, and concentrated HCl is used to acidify the solution pH to 1.0. The solution is extracted with 200 ml of EtOAc, and the organic layer is washed with 2×100 ml of water and 1×100 ml of brine. The organic layer is dried over $MgSO_4$ and concentrated to yield 1.5 g of the desired product as an off-white solid.

Preparation 8: 3-(4-Methanesulfonyl-benzyl)-4-oxo-3,4-dihydro-quinazoline-6-carboxylic acid

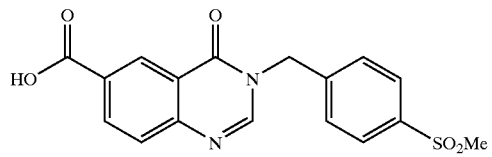

The compound is obtained according to the procedure described in Preparation 7 but using in Step 1 the compound obtained in Preparation 3 in which 4-methanesulfonyl-benzylamine is used in place of 4-fluorobenzylamine in the Step 2.

Preparation 9: 3-[4-(Pyrrolidine-1-sulfonyl)-benzyl]-4-oxo-3,4-dihydro-quinazoline-6-carboxylic acid

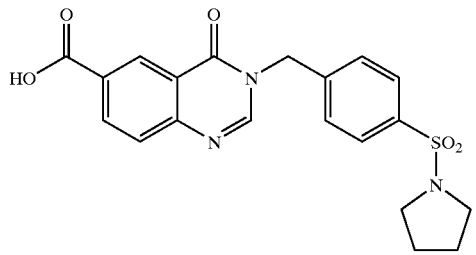

The compound is obtained according to the procedure described in Preparation 7 but using in step 1 the compound obtained in Preparation 3 in which 4-(pyrrolidine-1-sulfonyl)-benzylamine is used in place of 4-fluorobenzyl-amine in the Step 2.

Preparation 10: tert-butyl 4-(6-iodo-4-oxo-4H-quinazolin-3-ylmethyl)-benzoate

Step 1: 2-Amino-5-iodo-benzamide

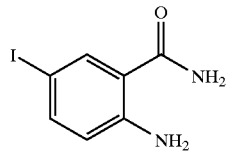

2.0 g (6.90 mmol) of the compound obtained in Step 1 of Preparation 3 is dissolved in approximately 50 ml of DMF, and an excess amount of aqueous ammonium hydroxide is added. After 10 minutes of stirring, the reaction solution is poured into 100 ml of water, and acidified with concentrated HCl, then extracted with 2×100 ml of EtOAc. The combined organic layer is then concentrated to yield 1.8 g (100%) of the desired product as an off-white powder.

N.M.R (DMSO-$d_6$) $^1$H δ (ppm): 6.50 (d, J=8.8 Hz, 1H), 6.68 (s, 2H), 7.12 (s, 1H), 7.33 (dd, $J_1$=8.8 Hz, $J_2$=2.1 Hz, 1H), 7.77 (d, J=1.9 Hz, 2H).

Step 2: 6-Iodo-3H-quinazolin-4-one

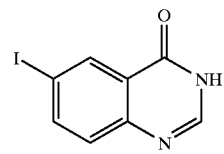

1.8 g (6.90 mmol) of compound obtained in the preceding Step 1 is suspended in 30 ml of triethyl orthoformate. A catalytic amount of para-toluene sulfonic acid is added, and the suspension is refluxed for 3 hours. All volatiles are removed in vacuo, and the residue is washed with 1:1 dichloromethane:Hexane to yield 1.5 g (80%) of an off white powder as the desired product.

MS(APCI), M/z 270.9 (M−1).

N.M.R (DMSO-$d_6$) $^1$H δ (ppm): 7.42 (d, J=8.5 Hz, 1H), 8.09 (dd, $J_1$=8.5 Hz, $J_2$=2.2 Hz, 1H), 8.09 (s, 1H), 8.34 (d, J=2.2 Hz, 1H), 12.38 (broad s, 1H).

Step 3: tert-Butyl 4-(6-Iodo-4-oxo-4H-quinazolin-3-ylmethyl)-benzoate

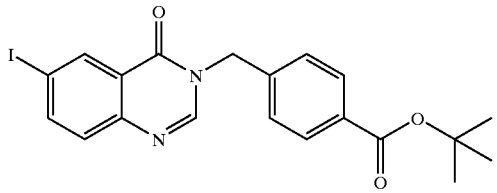

0.9 g (3.31 mmol) of compound obtained in the preceding Step 2 is dissolved in 50 ml of DMF. 1.18 g (3.64 mmol) of cesium carbonate and 0.986 g (3.64 mmol) of ter-butyl 4-bromomethyl-benzoate is added. The reaction is stirred at room temperature for 24 hours. 200 ml of EtOAc is then added, and then washed with 3×100 ml of water. The organic layer is dried over MgSO$_4$ and concentrated. The residue is purified on a silica gel column using 4:1 dichloromethane:hexane increasing gradually to a 1:1 ratio, to yield 0.97 g (62%) of white powder as the desired product.

MS(APCI), M/z 270.9 (M−1).

N.M.R (CDCl$_3$) $^1$H δ (ppm) 5.21 (s, 2H), 7.36 (d, J=8.5 Hz, 2H), 7.43 (d, J=8.5 Hz, 1H), 7.96 (dd, $J_1$=6.6 Hz, $J_2$=3.1 Hz, 2H), 8.01 (dd, $J_1$=6.5 Hz, $J_2$=2.1 Hz, 1H), 8.07 (s, 1H), 8.64 (d, J=1.8 Hz, 1H).

Example 1

3-(4-Methoxy-benzyl)-4-oxo-3,4-dihydro-quinazoline-6-carboxylic acid 4-methoxy-benzylamide

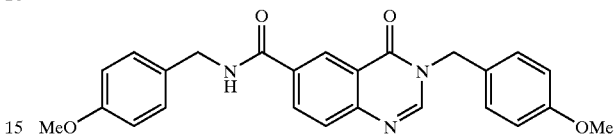

0.42 g (1.0 mmol) of the compound of Preparation 1 and 2.1 ml (1.85 g, 12.5 mmol) of triethylorthoformate are stirred for 20 hours at 160° C. After cooling, the precipitate obtained are filtered off, and recrystallized from acetonitrile to yield 0.180 g (yield=42%) of the desired compound.

TLC: CH$_2$Cl$_2$/MeOH 90/10 Rf=0.46.

N.M.R (DMSO-$d_6$) $^1$H δ (ppm): 3.75 (2s, 6H); 4.40 (d, 2H); 5.15 (s, 2H); 6.85–6.95 (m, 4H); 7.25 (d, 2H); 7.35 (d, 2H); 7.75 (d,1H); 8.25 (d,1H); 8.65 (s, 1H); 8.70 (s, 1H); 9.25 (t, 1H).

IR: 3282, 1661, 1606, 1513, 1248, 1032, 841 cm$^{-1}$.

MP=169° C.

PURITY: HPLC=96.7%

Example 2

3-(4-Methoxy-benzyl)-2-methyl-4-oxo-3,4-dihydro-quinazoline-6-carboxylic acid 4-methoxy-benzylamide, hydrochloride

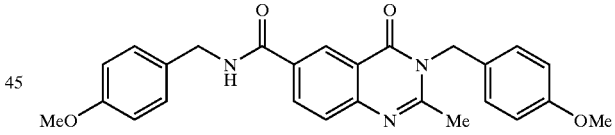

0.42 g (1.0 mmol) of the compound of Preparation 1, 1 ml of ethanol at 6% of HCl and 103 µl (100 mg, 1 mmol) of acetylacetone are stirred and then heated overnight under reflux. After cooling, the precipitate obtained are filtered off, and recrystallized from acetonitrile to yield the desired compound.

TLC: CH$_2$Cl$_2$/MeOH 90/10 Rf=0.56

N.M.R (DMSO-$d_6$) $^1$H δ (ppm): 2.70 (s, 3H); 3.75 (s, 6H); 4.45 (d, 2H); 5.35 (s, 2H); 6.85–6.95 (m, 4H); 7.20–7.30 (m, 4H); 7.30–7.80 (bs, 1H) 7.80(d, 1H); 8.35 (d, 1H); 8.70 (s, 1H); 9.35 (t, 1H).

IR: 3282, 1702, 1648, 1634, 1547, 1512, 1250, 1178, 1035, 793 cm$^{-1}$.

MP=208° C.

PURITY: HPLC=98.9%

Example 3

3-(4-Methoxy-benzyl)-1-methyl-4-oxo-1,2,3,4-tetrahydro-quinazoline-6-carboxylic acid 4-methoxy-benzylamide

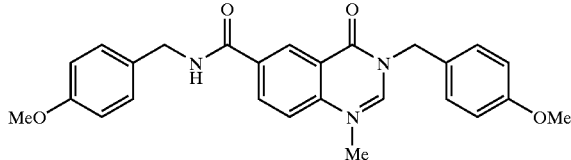

To a stirred solution of 0.42 g (1 mmol) of the compound of Preparation 1 in 2 ml of methanol are added 75 µl (1 mmol) of formaldehyde. The solution obtained is refluxed for 1 hour. Then 820 µl of a solution of NaOH 2M are added, and the reflux is maintained for 20 minutes. After cooling, water is added and the solution extracted with ethyl acetate. The organic layer is decanted, dried and concentrated under vacuum. The crude product (0.32 g 0.75 mmol) is dissolved into 3 ml of anhydrous DMF and stirred under inert atmosphere. 35 mg (0.09 mmol) of NaH are added to this solution and the yellow solution obtained is stirred for 30 minutes at room temperature and then 55 µl (125 mg, 0.9 mmol) of methyl iodide are added. After 30 minutes stirring, the reaction mixture is treated as usual and chromatographied over silica gel (dichloromethane/ether) to give the desired compound.

N.M.R (DMSO-$d_6$) $^1$H δ (ppm): 2.85 (s, 3H); 3.70 (s, 6H); 4.40 (d, 2H); 4.50 (s, 2H); 4.60 (s, 2H); 6.80–6.95 (m, 5H); 7.20–7.30 (m, 4H); 7.95 (d, 1H); 8.35 (s, 1H); 8.90 (t, 1H).

IR: 1637, 1511, 1467, 1247, 1175 cm$^{-1}$.

MP=182° C.

PURITY: HPLC=95.6%.

Example 4

3-(4-Methoxy-benzyl)-1,2,2-trimethyl-4-oxo-1,2,3,4-tetrahydro-quinazoline-6-carboxylic acid 4-methoxy-benzylamide

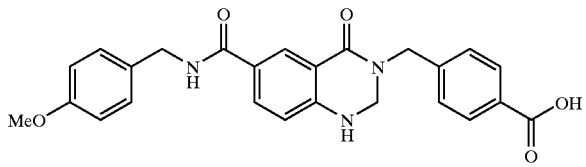

5 mg of para-toluenesulfonic acid are added to a stirred solution of 0.42 g of the compound of preparation 1 in 3 ml of acetone. The reaction mixture is stirred overnight at room temperature. This process is repeated to obtain a complete reaction. The solution is concentrated under vacuum and the crude product is methylated by addition of methyl iodide in the presence of NaH as described in Example 3. After purification by chromatography, the product obtained is crystallized in a mixture of dichloromethane and ether to give the desired compound.

TLC: CH$_2$Cl$_2$/Aceton 90/10 Rf=0.36.

N.M.R (DMSO-$d_6$) $^1$H δ (ppm): 1.40 (s, 6H); 2.90 (s, 3H); 3.75 (s, 6H); 4.40 (d, 2H); 4.80 (s, 2H); 6.80–6.90 (m, 4H); 6.95 (d, 1H); 7.20–7.30 (m, 4H); 7.90 (d, 1H); 8.40 (s, 1H); 8.90 (t, 1H).

IR: 1638, 1608, 1511, 1499, 1299, 1249, 1174 cm$^{-1}$.

MP=168° C.

PURITY: HPLC=96.4%.

Example 5

4-[6-(4-Methoxy-benzylcarbamoyl)-4-oxo-1,4-dihydro-2H-quinazolin-3-ylmethyl]-benzoic acid

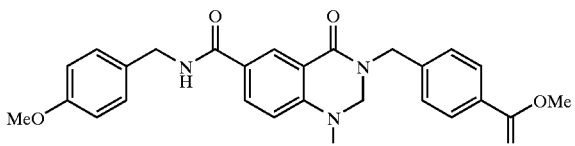

The compound is obtained according to the procedure described in the first step of Example 3 using as substrate the compound obtained in the Preparation 2.

TLC: CH$_2$Cl$_2$/MeOH 90/10 Rf=0.10.

N.M.R (DMSO-$d_6$) $^1$H δ (ppm): 3.70 (s, 3H); 4.35 (d, 2H); 4.60 (s, 2H); 4.70 (s, 2H); 6.75 (d, 1H); 6.85 (d, 2H); 7.20–7.30 (m, 3H); 7.45 (d, 2H); 7.80 (d, 1H); 7.90 (d, 2H); 8.30 (s, 1H); 8.85 (t, 1H); 12.85 (bs, 1H).

IR: 3314, 1678, 1629, 1513, 1294, 1248 cm$^{-1}$.

MP=270° C.

PURITY: HPLC=97.9%.

Example 6

Methyl 4-[6-(4-Methoxy-benzylcarbamoyl)-1-methyl-4-oxo-1,4-dihydro-2H-quinazolin-3-ylmethyl]-benzoate The compound is obtained according to the procedure described in the second step of Example 3 using as substrate the compound obtained in the Example 5.

TLC: CH$_2$Cl$_2$/MeOH 90/10 Rf=0.70.

N.M.R (DMSO-$d_6$) $^1$H δ (ppm): 2.85 (s, 3H); 3.70 (s, 3H); 3.85 (s, 3H); 4.40 (d, 2H); 4.55 (s, 2H) 4.75 (s, 2H); 6.80–6.90 (m, 3H); 7.25 (d, 2H); 7.45 (d, 2H); 7.95 (m, 3H); 8.35 (s, 1H); 8.90 (t, 1H).

IR: 3370, 1720, 1651, 1631, 1608, 1514, 1475, 1275, 1246, 1111 cm$^{-1}$.

MP=175° C.

PURITY: HPLC=94.5%.

Example 7

4-[6-(4-Methoxy-benzylcarbamoyl)-1-methyl-4-oxo-1,4-dihydro-2H-quinazolin-3-ylmethyl]-benzoic acid

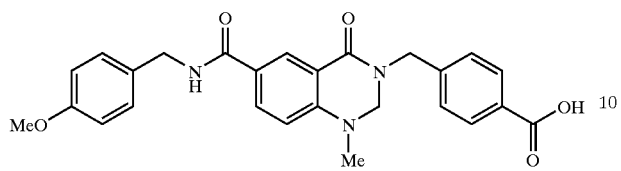

The compound is obtained according to the procedure described in the Step 2 of Preparation 5 using as substrate the compound of Example 6.

TLC: $CH_2Cl_2$/MeOH 90/10 Rf=0.35.

N.M.R (DMSO-$d_6$) $^1H$ δ (ppm): 2.85 (s, 3H); 3.70 (s, 3H); 4.40 (d, 2H); 4.55 (s, 2H); 4.75 (s, 2H); 6.80–6.90 (m, 3H); 7.25 (d, 2H); 7.45 (d, 2H); 7.95–8.00 (m, 3H); 8.40 (s, 1H); 8.90 (t, 1H); 12.90 (bs, 1H).

IR: 3540, 2740, 1709, 1637, 1513, 1476, 1313, 1245, 1173 cm$^{-1}$.

MP=124° C.

PURITY: HPLC=95.4%.

Example 8

3-(4-fluorobenzyl)-6-(3-phenyl-pro-1-ynyl)-3 H-quinazolin-4-one

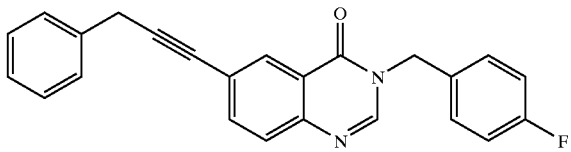

To a THF solution of the compound of Preparation 3 (153 mg, 0.40 mmol) and benzylacetylenylstannane (freshly prepared by addition of n-BuLi to the −78° C. solution of benzylacetylene, followed by quenching with tributyltin chloride) is added catalytic amount of $PdCl_2(Ph_3P)_2$ and CuI. The resulting suspension is refluxed for 1 hour and cooled to room temperature. After filtration and removal of volatiles in vacuo, the residue is purified using flash chromatography to give the desired compound as a white solid (80 mg, 54%).

N.M.R (CDCl$_3$) $^1H$ δ (ppm) 3.87 (s, 2H), 5.15 (s, 2H), 7.15 (t, J=8.3 Hz, 1H), 7.26–7.43 (m, 5H), 7.62 (d, J=8.3 Hz, 1H), 7.77 (dd, J=8.3, 1.9 Hz, 1H), 8.08 (s, 1H), 8.39 (d, J=1.9 Hz, 1H);

MS (APCI), M/z 369.5 (M+1).

Example 9

Methyl 4-[4-Oxo-6-(3-phenyl-prop-1-ynyl)-4H-quinazolin-3-ylmethyl]-benzoate

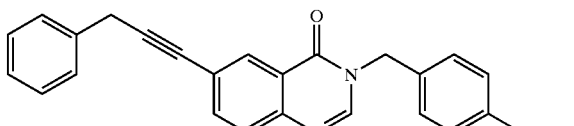

To a THF solution of the compound of Preparation 4 (165 mg, 0.39 mmol) and benzylacetylenylstannane (239 mg, 0.59 mmol, freshly prepared by addition of n-BuLi to the −78° C. solution of benzylacetylene, followed by quenching with tributyltin chloride) is added catalytic amount of $Pd(PPh_3)_2Cl_2$ and CuI. The resulting suspension is refluxed for 1 hour. After filtration and removal of volatiles in vacuo, the residue is purified using flash chromatography to give the desired compound as a white solid.

N.M.R (CDCl$_3$) $^1H$ δ (ppm): 3.85 (s, 2H), 3.89 (s, 3H), 5.23 (s, 2H), 7.40 (m, 5H), 7.80 (s, 1H), 8.00 (d, J=8.3 Hz, 2H), 8.40 (s, 1H).

MS (APCI), M/z 409.5 (M+1).

Example 10

4-[4-Oxo-6-(3-phenyl-prop-1-ynyl)-4H-quinazolin-3-ylmethyl]-benzoic acid

Step 1: 4-(6-Iodo-4-oxo-4H-quinazolin-3-ylmethyl)-benzoic acid

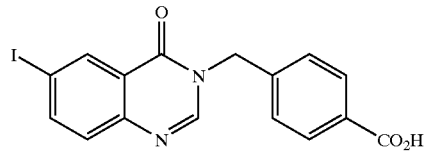

To a solution of the compound of Preparation 4 (2.25 g, 5.36 mmol) in 10% $H_2O$ in THF is added LiOH (2.25 g, 53.6 mmol). The reaction is stirred overnight at room temperature. After acidification using concentrated HCl, the reaction mixture is extracted with EtOAc. The organic layer is washed with water and brine, dried (MgSO$_4$), filtered and concentrated in vacuo. The crude product is triturated using a mixture of hexane/EtOAc: 4/1 to yield 2.00 g of the desired carboxylic acid as a white powder.

N.M.R (DMSO-$d_6$) $^1H$ δ (ppm): 5.23 (s, 2H), 7.40 (d, J=8.3 Hz, 2H), 7.47 (d, J=8.6 Hz, 1H), 7.87 (d, J=8.1, 2H), 8.1 (dd, J$_1$=8.6 Hz, J$_2$=1.9 Hz, 1H) 8.38 (d, J=1.7 Hz, 1H), 8.59 (s, 1H), 12.94 (br s, 1H).

MS (APCI), M/z 404.9 (M−1).

Step 2: 4-[4-Oxo-6-(3-phenyl-prop-1-ynyl)-4H-quinazolin-3-ylmethyl]-benzoic acid

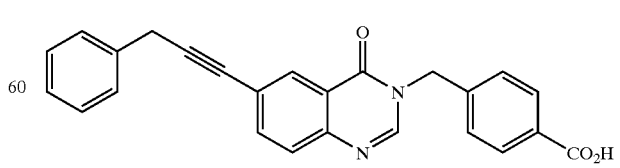

To a solution of the compound obtained in Step 1 (0.3 g, 0.739 mmol) in 6.5 ml of DMF, is added diisopropylethylamine (0.381 g, 2.96 mmol), CuI (catalytic amount), 3-phenyl-1-propyne (0.120 g, 1.03 mmol), and Pd(PPh$_3$)$_2$Cl$_2$ (catalytic amount). The reaction mixture is heated to 50° C. for 4 hours. The mixture is then diluted with 150 ml of EtOAc, and washed with 3×100 ml of water, 1×100 ml of brine. The organic layer is then dried over MgSO$_4$, and filtered. The filtrate is concentrated in vacuo. The crude product is triturated with a mixture of hexane/ethyl acetate: 8/1 to yield 225 mg of the pure desired product as a light yellow solid.

N.M.R (DMSO-d$_6$) $^1$H δ (ppm): 3.91 (s, 2H), 5.23 (s, 2H), 7.23–7.43 (m, 9H), 7.66 (d, J=8.3 Hz, 1H), 7.83 (dd, J$_1$=8.6 Hz, J$_2$=1.7 Hz, 1H), 7.87 (br s, 1H), 8.09 (d, J=1.6 Hz, 1H), 8.58 (s, 1H).

MS (APCI), M/z 395.1 (M$^+$1).

Example 11

3-(4-fluorobenzyl)-6-(3-phenyl-prop-1-ynyl)-3H-pyrido[3,4-d]pyrimidin-4-one

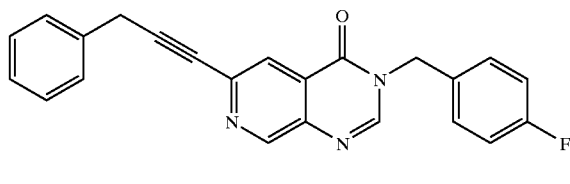

To a THF solution of a compound of Preparation 5 (0.40 mmol) and benzylacetylenyl stannane (freshly prepared by addition of n-BuLi to the −78° C. solution of benzylacetylene, followed by quenching with tributyltin chloride) is added a catalytic amount of PdCl$_2$(Ph$_3$P)$_2$ and CuI. The resulting suspension is refluxed for 1 hour, and cooled to room temperature. After filtration and removal of volatiles in vacuo, the residue is purified using flash chromatography on silica gel to give the desired compound.

Example 12

Methyl 4-[6-(3-phenyl-prop-1-ynyl)-4-oxo-4H-pyrido[3,4-d]pyrimidin-3-ylmethyl]-benzoate

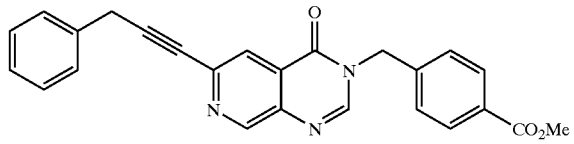

To a THF solution of the compound of Preparation 6 (0.39 mmol) and benzylacetylenylstannane (239 mg, 0.59 mmol), freshly prepared by addition of n-BuLi to the −78° C. solution of benzylacetylene, followed by quenching with tributyltin chloride) is added catalytic amount of PdCl$_2$(Ph$_3$P)$_2$ and CuI. The resulting suspension is refluxed for 1 hour. After filtration and removal of volatile in vacuo, the residue is purified using flash chromatography to give the desired product.

Example 13

4-[6-(3-phenyl-prop-1-ynyl)-4-oxo-4H-pyrido[3,4-d]pyrimidin-3-ylmethyl]-benzoic acid Step 1: 4-(6-Iodo-4-oxo-4H-pyrido[3,4-d]pyrimidin-3-ylmethyl)-benzoic acid

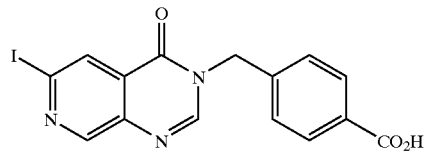

To a solution of the compound of Preparation 6 (5.36 mmol), in 10% H$_2$O in THF is added LiOH (2.25 g, 53.6 mmol). The reaction is stirred overnight at room temperature. After acidification using concentrated HCl, the reaction mixture is extracted with EtOAc. The organic layer is washed with water and brine, dried (MgSO$_4$) and filtered in vacuo. The crude product is triturated using 4/1 hexane/EtOAc to give the desired compound.

Step 2: 4-[6-(3-phenyl-prop-1-ynyl)-4-oxo-4H-pyrido[3,4-d]pyrimidin-3-ylmethyl]-benzoic acid

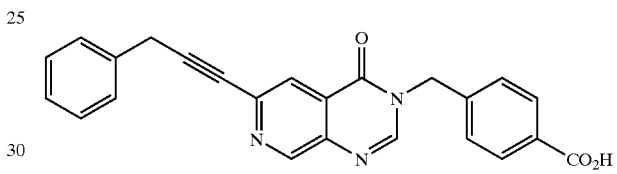

To a solution of the compound obtained in Step 1 (0.739 mmol) in 6.5 ml of DMF, is added diisopropylethylamine (0.381 g, 2.96 mmol), CuI (catalytic amount), 3-phenyl-1-propyne (0.120 g, 1.03 mmol), and Pd(PPh$_3$)$_2$Cl$_2$ (catalytic amount). The reaction mixture is warmed to 50° C. for 4 hours. The mixture is then diluted with 150 ml of EtOAc, and washed with 3×100 ml of water, 1×100 ml of brine. The organic layer is then dried over MgSO$_4$ and filtered. The filtrate is concentrated in vacuo. The crude product is triturated with 8/1: hexane/EtOAc to yield the desired compound.

Example 14

3-(4-Fluoro-benzyl)-4-oxo-3,4-dihydro-quinazoline-6-carboxylic acid 3-methoxy-benzylamide

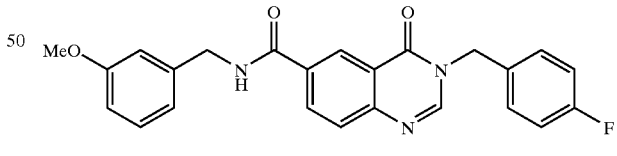

0.2 g (0.671 mmol) of the compound obtained in the Preparation 7 is dissolved in 50 ml of chloroform. 110 mg of 3-methoxybenzyl amine, 205 mg of Mukaiyama reagent and 163 mg of triethylamine is added. The reaction solution is then stirred at room temperature overnight. The reaction solution is concentrated and purified on silica gel column with 1:1 Hexane:EtOAc to yield 150 mg of the desired product as an off white solid.

N.M.R (CDCl$_3$) $^1$H δ (ppm): 3.79 (s, 3H), 4.62 (d, J=5.6 Hz, 2H), 5.13 (s, 2H), 6.63 (s, 1H), 6.81–7.34 (m, 8 H), 7.75 (d, J=8.6 Hz, 1H), 8.13 (s, 1H), 8.30 (dd, J$_1$=8.6 Hz, J$_2$=2.2 Hz, 1H), 8.56 (d, J=2.0 Hz, 1H).

Example 15

3-(4-Methanesulfonyl-benzyl-4-oxo-3,4-dihydro-quinazoline-6-carboxylic acid 4-methoxy-benzylamide

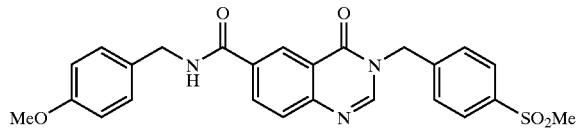

The compound is obtained according to the procedure described in Example 14 using as substrate the compound obtained in Preparation 8 and 4-methoxybenzylamine.

MS(APCI), M/z 478.1 (M+1).

N.M.R (DMSO-$d_6$) $^1$H δ (ppm): 3.18 (s, 3H), 3.72 (s, 3H), 4.39 (d, J=5.1 Hz, 2H), 5.18 (s, 2H), 6.87 (d, J=8.3 Hz, 2H), 7.23 (d, J=8.1 Hz, 2H), 7.25 (s, 1H), 7.56 (d, J=8.3 Hz, 2H), 7.85 (d, J=8.1 Hz, 2H), 8.16 (d, J=8.7 Hz, 1H), 8.51 (s, 1H), 9.15 (s, 1H).

Example 16

4-Oxo-3-[4-(pyrrolidine-1-sulfonyl)-benzyl]-3,4-dihydro-quinazoline-6-carboxylic acid 4-methoxy-benzylamide

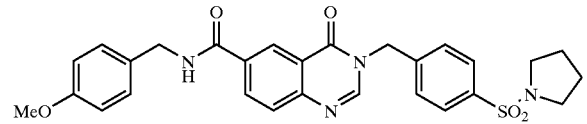

The compound is obtained according to the procedure described in Example 14 using as substrate the compound obtained in Preparation 9 and 4-methoxybenzylamine.

MS(APCI), M/z 533.2 (M+1).

N.M.R (DMSO-$d_6$) $^1$H δ (ppm): 1.59 (s, 4H), 3.07 (s, 4H), 3.68 (s, 3H), 4.39 (d, J=5.5 Hz, 2H), 5.29 (s, 2H), 6.85 (d, J=8.3 Hz, 2H), 7.23 (d, J=8.0 Hz, 2H), 7.25 (s, 1H), 7.54 (d, J=8.1 Hz, 2H), 7.74 (d, J=8.1 Hz, 2H), 8.26 (d, J=8.3 Hz, 1H), 8.64 (s, 1H), 8.66 (s, 1H), 9.27 (s, 1H).

Example 17

4-[6-(3-Methoxy-benzylcarbamoyl)-4-oxo-4H-quinazolin-3-ylmethyl]-benzoic acid

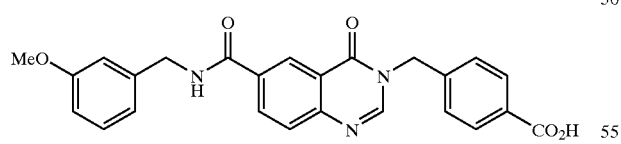

The desired product is obtained by following the procedure of Example 14, except 4-flurobenzylamine in step 2 of the preparation 3 is replaced by tert-butyl 3-aminomethyl-benzoate, and at the end stirring the collected residue in an excess amount of trifluoroacetic acid for 30 minutes at room temperature. After removing the volatiles in vacuum, the residue is filtered to furnish the desired product as an off white solid.

N.M.R (DMSO-$d_6$) $^1$H δ (ppm): 3.71 (s, 3H), 4.43 (d, J=4.6 Hz, 2H), 5.15 (s, 2H), 6.79 (d, J=7.6 Hz, 1H), 6.86 (s, 2H), 7.20–7.26 (m, 2H), 7.40 (d, J=7.3 Hz, 2H), 7.86 (d, J=7.6 Hz, 2H), 8.16 (d, J=8.1 Hz, 1H), 8.53 (s, 1H), 9.20 (s, 1H), 11.80 (s, 1H).

Example 18

4-[4-oxo-6-(3-phenyl-prop-1-ynyl)-4H-quinazoline-3-ylmnethyl]-benzoic acid

Step 1: tert-Butyl 4-[4-oxo-6-(3-phenyl-prop-1-ynyl)-4H-quinazoline-3-ylmethyl]-benzoate

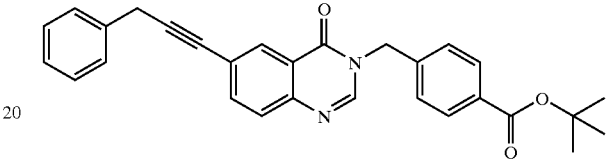

3.0 g (6.48 mmol) of the compound of Preparation 10 is dissolved in 50 ml of DMF. 3.34 g (25.9 mmol) of diisopropylethylamine, catalytic amount of copper(I)iodide, 3.01 g (25.9 mmol) 3-phenyl-1-propyne and catalytic amount of Pd(PPh$_3$)$_2$Cl$_2$ is then added in that order. The reaction solution is stirred at 50° C. for 24 hours, then diluted with 300 ml of EtOAc and washed with 3×200 ml of water, 1×200 ml of brine. The organic layer is dried over MgSO$_4$ and concentrated. The residue is purified on silica gel column with 4:1 Hexane:EtOAc gradually increasing to 1:1 Hexane:EtOAC to yield a waxy substance as the desired product.

N.M.R (DMSO-$d_6$) $^1$H δ (ppm): 1.50 (s, 9H), 5.24 (s, 2H), 7.42 (d, J=8.8 Hz, 2H), 7.49 (d, J=8.6 Hz, 1H), 7.84 (d, J=8.6 Hz, 2H), 8.11 (dd, J$_1$=8.6 Hz, J$_2$=2.2 Hz, 1H), 8.39 (d, J=2.0 Hz, 1H), 8.59 (s, 1H).

Step 2: 4-[4-oxo-6-(3-phenyl-prop-1-ynyl)-4H-quinazoline-3-ylmethyl]-benzoic acid

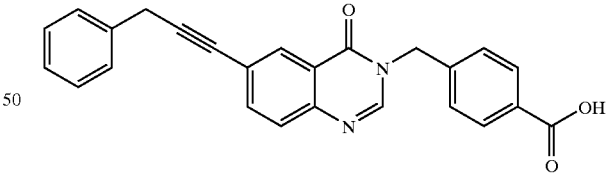

An excess amount (20 ml) of trifluroacetic acid is added to the compound obtained in the preceding Step 1. After 30 minutes of stirring, all volatiles are removed and the residue triturated with 1:1 Hexane:EtOAc. The precipitate is collected via filtration and washed with a small amount of methanol to yield 1.82 g of the desired product as an off-white solid.

N.M.R (DMSO-$d_6$) $^1$H δ (ppm): 3.91 (s, 2H), 5.23 (s, 2H), 7.23–7.43 (m, 9H), 7.66 (d, J=8.3 Hz, 1H), 7.83 (dd, J$_1$=8.6 Hz, J$_2$=1.7 Hz, 1H), 7.87 (broad s, 1H), 8.09 (d, J=1.6 Hz, 1H), 8.58 (s, 1H).

Example 19

4-{6-[3-(4-Methoxy-phenyl)-prop-1-ynyl]-4-oxo-4H-quinazoline-3-ylmethyl}-benzoic acid

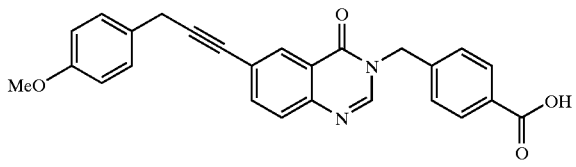

The product is obtained by following the procedure of Example 18, the only difference is that 3-phenyl-1-propyne used in Step 1 is replaced by 1-methoxy-4-prop-2-ynyl-benzene. The product is obtained as a white solid.

N.M.R (DMSO-$d_6$) $^1$H δ (ppm): 3.70 (s, 3H), 3.83 (s, 2H), 5.24 (s, 2H), 6.89 (d, J=8.5 Hz, 2H), 7.29 (d, J=8.3 Hz, 2H), 7.41(d, J=8.0 Hz, 2H), 7.65 (d, J=8.3 Hz, 1H), 7.81 (dd, $J_1$=8.3 Hz, $J_2$=1.5 Hz, 1H), 7.88 (d, J=8.1 Hz, 2H), 8.08 (d, J=1.5 Hz, 1H), 8.58 (s, 1H), 12.94 (broad s, 1H).

Example 20

4-[4-oxo-6-(3-phenyl-prop-1-ynyl)-4H-quinazoline-3-ylmethyl]-benzamide

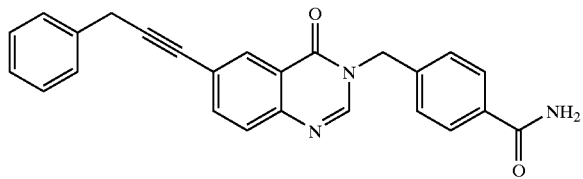

0.1 g (0.254 mmol) of the compound of Example 18 is suspended in 50 ml of dichloromethane. 35.4 mg of oxalyl chloride (0.279 mmol) is added, followed by 1 drop of DMF. The reaction is refluxed under nitrogen for 2 hours, and stirred at room temperature for an additional 12 hours. Then an excess amount of 0.5 M ammonia in dioxane is added. The reaction is stirred at room temperature for 1 hour. The solvent is then removed in vacuum and the residue is washed with 1:1 water:methanol to yield 70 mg of an off-white powder as the desired product.

MS(APCI), M/z 394.1 (M$^+$1).

N.M.R (DMSO-$d_6$) $^1$H δ (ppm): 3.92 (s, 2H), 5.21 (s, 2H), 7.24–7.39 (m, 9H), 7.66 (d, J=8.5 Hz, 1H), 7.80–7.92 (m, 4H), 8.10 (s, 2H), 8.58 (s, 1H).

Example 21

3-(4-Fluoro-benzyl)-4-oxo-3,4-dihydro-quinazoline-6-carboxylic acid (2-methoxy-pyridin-4-ylmethyl)-amide

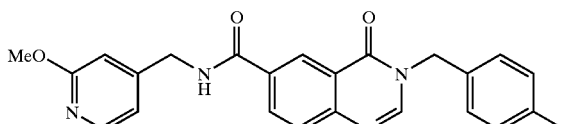

Compound of the Preparation 7 (227 mg, 0.76 mmol), 2-methoxy-pyridin-4-yl-methylamine (138 mg, 1.0 mmol) and the Mukaiyama reagent (256 mg, 1.0 mmol) are dissolved in CHCl$_3$ (10 ml), Et$_3$N (1 ml, excess) is added. The resulting solution is refluxed for 3 h, cooled to room temperature. The solution is then purified via a flash chromatography to give the desired product as a white solid, 34 mg, 63% yield.

MS (APCI), M/z 419.2 (M+1).

N.M.R (DMSO-$d_6$) $^1$H δ (ppm): 9.40 (t, J=5.9 Hz, 1H), 8.70 (s, 1H), 8.69 (s, 1H), 8.28 (dd, 1H), 8.07 (d, J=5.4 Hz, 1H), 7.77 (d, J=8.3 Hz, 1H), 7.44 (m, 1H), 7.19 (t, J=8.7 Hz, 1H), 6.91 (d, J=5.1 Hz, 1H), 6.69 (s, 1H), 5.19 (s, 2H), 4.45 (d, J=5.9 Hz, 1H), 3.80 (s, 3H)

Example 22

3-[(3,5-difluoro-4-hydroxy)-benzyl]-6-(3-phenyl-prop-1-ynyl)-3H-quinazolin-4-one

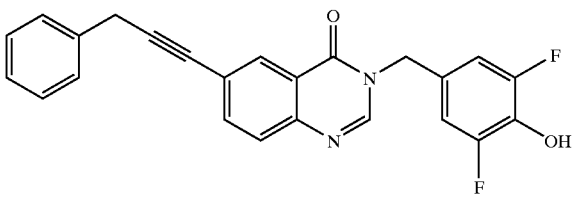

To a solution of 3-[(3,5-difluoro-4-hydroxy)-benzyl]-6-iodo-3H-quinazolin-4-one (obtained following the procedure of preparation 3 but using in step 2 (3,5-difluoro-4-hydroxy)-benzylamine) (0.3 g, 720 mmol) in 6.5 ml of DMF, is added diisopropylethyl amine (0.381 g, 2.96 mmol), 3-phenyl-1-propyne (0.34 g, 2.9 mmol), CuI (catalytic amount), and Pd(PPh$_3$)$_2$Cl$_2$ (catalytic amount). The reaction mixture is heated to 50° C. for 4 hours. The mixture is then diluted with 150 ml of EtOAc, and washed with 3×100 ml of water, 1×100 ml of brine. The organic layer is then dried over MgSO$_4$ and filtered. The filtrate is concentrated in vacuo. The crude product is purified via a flash chromatography to yield 225 mg of the pure desired product as a light yellow solid.

MS (APCI), M/z 403.1 (M+1).

N.M.R (DMSO-$d_6$) $^1$H δ (ppm): 8.46 (s, 1H), 8.25 (d, J=2.0 Hz, 1H), 7.1–7.8 (m, 9H), 5.20 (s, 2H), 3.91 (s, 2H).

Example 23

3-(3-Fluoro-benzyl)-4-oxo-3,4-dihydro-pyrido[3,4-d]pyrimidine-6-carboxylic acid 3-methoxy-benzylamide Step 1: 6-Chloro-3-(3-fluoro-benzyl)-3H-pyrido[3,4-d]pyrimidin-4-one

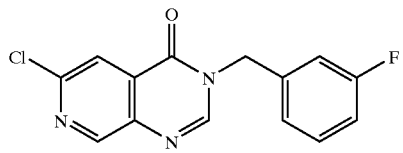

The starting material, 6-chloro-3H-pyrido[3,4-d]pyrimidin-4one (710 mg, 3.92 mmol, prepared according to *J. Chem. Soc., Perkin Trans.* 1996, 1, 2221) is dissolved in DMF (20 ml). Cs$_2$CO$_3$ (1.66 g, 5.1 mmol) and 3-flurobenzylchloride (737 mg, 5.1 mmol) are added subsequently. The reaction is stirred at room temperature overnight, poured into water. After extraction with CH$_2$Cl$_2$, the organic layer is washed with H₂O and brine, dried (Na₂SO₄) and filtered. After removal of the solvents, the residue is purified via a flash chromatography to give the product as a white solid.

MS (APCI), M/z 290.0 (M+1).

N.M.R (CDCl₃) ¹H δ (ppm) 8.92 (s, 1H), 8.10 (d, J=9.6 Hz, 2H), 7.0–7.4 (m, 5H), 5.17 (m, 2H).

Step 2: Methyl 3-(3-fluorobenzyl)-4-oxo-3,4-dihydro-pyrido[3,4-d]pyrimidine-6-carboxylate

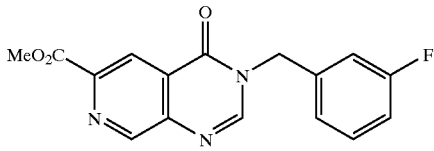

The compound obtained in the preceding Step 1 (3.0 g, 1.07 mmol), is dissolved in 50 ml of methanol, with an excess amount of triethylamine, and a catalytic amount of Pd(dppf)Cl₂. The reaction solution is poured into an autoclave and heated at 100° C. for 4 hours under the carbon monoxide atmosphere. The reaction is cooled to room temperature and filtered. The filtrate is concentrated in vacuum and the residue is purified on a silica gel column using 1:1 Hex:EtOAc to yield the desired product as a white solid (100%).

MS (APCI), M/z 314.0 (M+1).

N.M.R (CDCl₃) ¹H δ (ppm): 9.24 (s, 1H), 8.95 (s, 1H), 8.28 (s, 1H), 7.0–7.4 (m, 4H), 5.24 (s, 2H), 4.08 (s, 3H).

Step 3: 3-(3-Fluoro-benzyl)-4-oxo-3,4-dihydro-pyrido[3,4-d]pyrimidine-6-carboxylic acid 3-methoxy-benzylamide

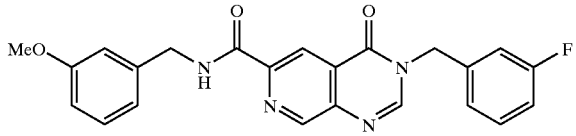

To a 0° C. solution of 3-methoxybenzylamine (144 mg, 1.05 mmol) in CH₂Cl₂ is added AlMe₃ (0.52 ml, 1.05 mmol). The reaction is stirred at room temperature for 2 h. Then a solution of the compound obtained in the preceding Step 2 (111 mg, 0.35 mmol) in CH₂Cl₂ is added and the resulting reaction is stirred at room temperature for 2 h, and poured into water. After extraction with CH₂Cl₂, the organic layer is washed with H₂O and brine, dried (Na₂SO₄) and filtered. After removal of the solvents, the residue is purified via a flash chromatography to give the product as a white solid.

MS (APCI), M/z 419.1 (M+1).

N.M.R (CDCl₃) ¹H δ (ppm): 9.40 (t, 1H), 9.09 (s, 1H), 8.76 (s, 1H), 8.54 (s, 1H), 6.7–7.4 (m, 11H), 5.22 (s, 2H), 4.45 (d, J=6.6 Hz, 1H), 3.67 (s, 3H)

Example 24

3-(3-Fluoro-benzyl)-4-oxo-3,4-dihydro-pyrido[3,4-d]pyrimidine-6-carboxylic acid 4-methoxy-benzylamide

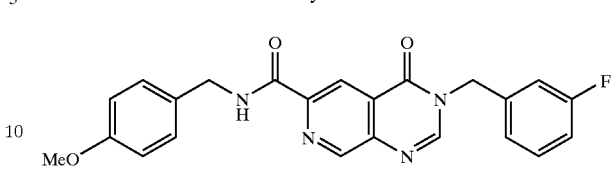

The compound is obtained according to the procedure of Example 23 using in the Step 3, 4-methoxybenzylamine.

MS (APCI), M/z 419.1 (M+1).

N.M.R (CDCl) ¹H δ (ppm): 9.40 (t, 1H), 9.09 (s, 1H), 8.76 (s, 1H), 8.54 (s, 1H), 7.0–7.4 (m, 9H), 6.80 (d, J=1.6 Hz, 2H), 5.22 (s, 2H), 4.45 (d, J=6.6 Hz, 1H), 3.67 (s, 3H)

Example 25

4-[4-Oxo-6-(3-phenyl-propa-1,2-dienyl)-4H-quinazolin-3-ylmethyl]-benzoic acid

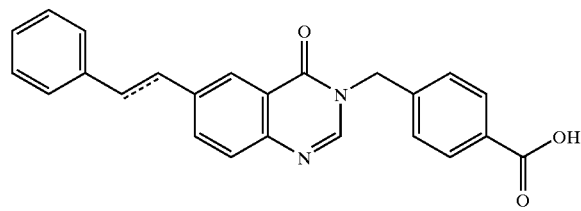

0.105 g (0.257 mmol) of the compound of Example 9 is dissolved in 25 ml of 90% THF:10% water. 10 equivalents of LiOH are added. The reaction is refluxed for 3 hours, 200 ml of EtOAc are added, acidified by concentrated HCl and the solution is washed with 2×100 ml of water and 1×100 ml of brine. Organic layer dried over MgSO₄, and concentrated. The residue is purified on a silica gel column with 95% EtOAc:5% MeOH to yield 30 mg of the product as a light yellow powder.

MS(APCI), M/z 481.2 (M+1)

N.M.R (DMSO-d₆) ¹H δ (ppm): 5.23 (s, 2H). 6.90 (d, J=6.6 Hz, 1H), 7.02(d, J=6.6 Hz, 1H), 7.24 (m, 1H), 7.33 (d, J=4.1, 4H), 7.40 (d, J=8.3 Hz, 2H), 7.65(d, J=8.3 Hz, 1H), 7.75 (dd, J₁=8.5 Hz, J₂=1.7 Hz, 1H), 7.87 (d, J=8.1 Hz, 2H), 8.07 (s, 1H), 8.53(s, 1H).

Examples 26 to 71

These compounds are obtained according to the procedure described in the Preparation 5 and Example 8 using the corresponding substrates and reagents.

26. 4-{6-[3-(4-Methoxy-phenyl)-prop-1-ynyl]-4-oxo-4H-quinazolin-3-ylmethyl}-benzoic acid,
27. 3-(4-Methanesulfonyl-benzyl)-6-[3-(4-methoxy-phenyl)-prop-1-ynyl]-3H-quinazolin-4-one,
28. 4-{6-[3-(3-Methoxy-phenyl)-prop-1-ynyl]-4-oxo-4H-quinazolin-3-ylmethyl}-benzoic acid,
29. 3-(4-Methanesulfonyl-benzyl)-6-[3-(3-methoxy-phenyl)-prop-1-ynyl]-3H-quinazolin-4-one,
30. 4-[4-oxo-6-(3-pyridin-4-yl-prop-1-ynyl)-4H-quinazolin-3-ylmethyl]-benzoic acid,
31. 3-(4-Methanesulfonyl-benzyl)-6-(3-pyridin-4-yl-prop-1-ynyl)-3H-quinazolin-4-one 32. 4-[4-oxo-6-(3-pyridin-3-yl-prop-1-ynyl)-4H-quinazolin-3-ylmethyl]-benzoic acid,
33. 3-(4-Methanesulfonyl-benzyl)-6-(3-pyridin-3-yl-prop-1-ynyl)-3H-quinazolin-4-one,
34. 4-{6-[3-(4-fluro-phenyl)-prop-1-ynyl]-4-oxo-4H-quinazolin-3-ylmethyl}-benzo acid,
35. 6-[3-(4-Fluro-phenyl)-prop-1-ynyl]-3-(4-methanesulfonyl-benzyl)-3H-quinazolin-4-one,
36. 4-{6-[3-(3-fluro-phenyl)-prop-1-ynyl]-4-oxo-4H-quinazolin-3-ylmethyl}-benzo acid,
37. 6-[3-(3-Fluro-phenyl)-prop-1-ynyl]-3-(4-methanesulfonyl-benzyl)-3H-quinazolin-4-one,
38. 4-{6-[3-(4-chloro-phenyl)-prop-1-ynyl]-4-oxo-4H-quinazolin-3-ylmethyl}-benzoic acid,
39. 6-[3-(4-Chloro-phenyl)-prop-1-ynyl]-3-(4-methanesulfonyl-benzyl)-3H-quinazolin-4-one,
40. 4-{6-[3-(3-chloro-phenyl)-prop-1-ynyl]-4-oxo-4H-quinazolin-3-ylmethyl}-benzoic acid,
41. 6-[3-(3-Chloro-phenyl)-prop-1-ynyl]-3-(4-methanesulfonyl-benzyl)-3H-quinazolin-4-one,
42. 4-{6-[3-(4-bromo-phenyl)-prop-1-ynyl]-4-oxo-4H-quinazolin-3-yl methyl}-benzoic acid,
43. 6-[3-(4-bromo-phenyl)-prop-1-ynyl]-3-(4-methanesulfonyl-benzyl)-3H-quinazolin-4-one,
44. 4-{6-[3-(3-bromo-phenyl)-prop-1-ynyl]-4-oxo-4H-quinazolin-3-ylmethyl}-benzoic acid,
45. 6-[3-(3-bromo-phenyl)-prop-1-ynyl]-3-(4-methanesulfonyl-benzyl)-3H-quinazolin-4-one,
46. 4-{6-[3-(4-nitro-phenyl)-prop-1-ynyl]-4-oxo-4H-quinazolin-3-ylmethyl}-benzoic acid,
47. 3-(4-Methanesulfonyl-benzyl)-6-[3-(4-nitro-phenyl)-prop-1-ynyl]-3H-quinazolin-4-one,
48. 4-{6-[3-(2-methoxy-pyridin-4-yl)-prop-1-ynyl]-4-oxo-4H-quinazolin-3-ylmethyl}-benzoic acid,
49. 3-(4-Methanesulfonyl-benzyl)-6-[3-(2-methoxy-pyridin-4-yl)-prop-1-ynyl]-3H-quinazolin-4-one,
50. 4-{6-[3-(4-methylsulfanyl-phenyl)-prop-1-ynyl]-4-oxo-4H-quinazolin-3-ylmethyl}-benzoic acid.
51. 3-(4-Methanesulfonyl-benzyl)-6-[3-(4-methylsulfanyl-phenyl)-prop-1-ynyl]-3H-quinazolin-4-one
52. 4-{6-[3-(3-methylsulfanyl-phenyl)-prop-1-ynyl]-4-oxo-4H-quinazolin-3-ylmethyl}-benzoic acid
53. 3-(4-Methanesulfonyl-benzyl)-6-[3-(3-methylsulfanyl-phenyl)-prop-1-ynyl]-3H-quinazolin-4-one
54. 4-[4-oxo-6-(3-p-tolyl-prop-1-ynyl)-4H-quinazolin-3-ylmethyl]-benzoic acid
55. 3-(4-Methanesulfonyl-benzyl)-6-(3-p-tolyl-prop-1-ynyl)-3H-quinazolin-4-one
56. 4-[4-oxo-6-(3-m-tolyl-prop-1-ynyl)-4H-quinazolin-3-ylmethyl]-benzoic acid
57. 3-(4-Methanesulfonyl-benzyl)-6-(3-m-tolyl-prop-1-ynyl)-3H-quinazolin-4-one
58. 4-[6-(3-Imidazol-1-yl-prop-1-ynyl)-4-oxo-4H-quinazolin-3-ylmethyl]-benzoic acid
59. 4-[4-Oxo-6-(3-phenyl-prop-1-ynyl)-4H-quinazolin-3-ylmethyl]-benzenesulfonamide
60. 4-[4-Oxo-6-(3-phenyl-prop-1-ynyl)-4H-quinazolin-3-ylmethyl]-benzonitrile
61. 3-(3-Chloro-benzyl)-6-(4-phenyl-but-1-ynyl)-3H-quinazolin-4-one
62. 3-(3-Chloro-benzyl)-6-(3-phenyl-prop-1-ynyl)-3H-quinazolin-4-one
63. 4-[4-Oxo-6-(3-pyrazol-1-yl-prop-1-ynyl)-4H-quinazolin-3-ylmethyl]-benzoic acid
64. 6-(3-Phenyl-prop-1-ynyl)-3-[4-(1H-tetrazol-5-yl)-benzyl]-3H-quinazolin-4-one
65. 3-(3,4-Difluoro-benzyl)-6-[3-(pyridin-4-yloxy)-prop-1-ynyl]-3H-quinazolin-4-one
66. 3-(3,4-Difluoro-benzyl)-6-[3-(4-methoxy-phenyl)-prop-1-ynyl]-3H-quinazolin-4-one
67. N-{4-[4-Oxo-6-(3-phenyl-prop-1-ynyl)-4H-quinazolin-3-ylmethyl]-phenyl}-acetamide
68. 3-(3,4-Difluoro-benzyl)-6-(3-phenyl-prop-1-ynyl)-3H-quinazolin-4-one
69. 3-(4-Acetyl-benzyl)-6-[3-(4-methoxy-phenyl)-prop-1-ynyl]-3H-quinazolin-4-one
70. 6-(3-Phenyl-prop-1-ynyl)-3-pyridin-4-ylmethyl-3H-quinazolin-4-one
71. 6-[3-(4-Methoxy-phenyl)-prop-1-ynyl]-3-pyridin-4-ylmethyl-3H-quinazolin-4-one Examples 72 to 103

These compounds are obtained according to the procedure described in the Preparation 6 and Example 11 using the corresponding substrates and reagents.

72. 4-{6-[3-(4-methoxy-phenyl)-prop-1-ynyl]-4-oxo-4H-pyrido[3,4-d]pyrimidin-3-ylmethyl}-benzoic acid,
73. 3-(4-methanesulfonyl-benzyl)-6-[3-(4-methoxyl-phenyl)-prop-1-ynyl]-3H-pyrido[3,4-d]pyrimidin-4-one,
74. 4-{6-[3-(3-methoxy-phenyl)-prop-1-ynyl]-4-oxo-4H-pyrido[3,4-d]pyrimidin-3-ylmethyl}-benzoic acid,
75. 3-(4-Methanesulfonyl-benzyl)-6-[3-(3-methoxyl-phenyl)-prop-1-ynyl]-3H-pyrido[3,4-d]pyrimidin-4-one,
76. 4-[4-oxo-6-(3-pyridin-4-yl-prop-1-ynyl)-4H-pyrido[3,4-d]pyrimidin-3-ylmethyl]-benzoic acid,
77. 3-(4-Methanesulfonyl-benzyl)-6-(3-pyridin-4-yl-prop-1-ynyl)-3H-pyrido[3,4-d]pyrimidin-4-one,
78. 4-[4-oxo-6-(3-pyridin-3-yl-prop-1-ynyl)-4H-pyrido[3,4-d]pyrimidin-3-ylmethyl]-benzoic acid,
79. 3-(4-Methanesulfonyl-benzyl)-6-(3-pyridin-3-yl-prop-1-ynyl)-3H-pyrido[3,4-d]pyrimidin-4-one,
80. 4-{6-[3-(4-fluro-phenyl)-prop-1-ynyl]-4-oxo-4H-pyrido[3,4-d]pyrimidin-3-ylmethyl}-benzoic acid,
81. 6-[3-(4-Fluro-phenyl)-prop-1-ynyl]-3-(4-methanesulfonyl-benzyl)-3H-pyrido[3,4-d]pyrimidin-4-one,
82. 4-{6-[3-(3-fluro-phenyl)-prop-1-ynyl]-4-oxo-4H-pyrido[3,4-d]pyrimidin-3-ylmethyl}-benzoic acid,
83. 6-[3-(3-Fluro-phenyl)-prop-1-ynyl]-3-(4-methanesulfonyl-benzyl)-3H-pyrido[3,4-d]pyrimidin-4-one,
84. 4-{6-[3-(4-chloro-phenyl)-prop-1-ynyl]-4-oxo-4H-pyrido[3,4-d]pyrimidin-3-ylmethyl}-benzoic acid,
85. 6-[3-(4-Chloro-phenyl)-prop-1-ynyl]-3-(4-methanesulfonyl-benzyl)-3H-pyrido[3,4-d]pyrimidin-4-one,
86. 4-{6-[3-(3-chloro-phenyl)-prop-1-ynyl]-4-oxo-4H-pyrido[3,4-d]pyrimidin-3-ylmethyl}-benzoic acid,
87. 6-[3-(3-Chloro-phenyl)-prop-1-ynyl]-3-(4-methanesulfonyl-benzyl)-3H-pyrido[3,4-d]pyrimidin-4-one,
88. 4-{6-[3-(4-bromo-phenyl)-prop-1-ynyl]-4-oxo-4H-pyrido[3,4-d]pyrimidin-3-ylmethyl}-benzoic acid,
89. 6-[3-(4-Bromo-phenyl)-prop-1-ynyl]-3-(4-methanesulfonyl-benzyl)-3H-pyrido[3,4-d]pyrimidin-4-one,
90. 4-{6-[3-(3-bromo-phenyl)-prop-1-ynyl]-4-oxo-4H-pyrido[3,4-d]pyrimidin-3-ylmethyl}-benzoic acid,
91. 6-[3-(3-Bromo-phenyl)-prop-1-ynyl]-3-(4-methanesulfonyl-benzyl)-3H-pyrido[3,4-d]pyrimidin-4-one,
92. 4-{6-[3-(4-nitro-phenyl)-prop-1-ynyl]-4-oxo-4H-pyrido[3,4-d]pyrimidin-3-ylmethyl}-benzoic acid,
93. 3-(4-Methanesulfonyl-benzyl)-6-[3-(4-nitro-phenyl)-prop-1-ynyl)-3H-pyrido[3,4-d]pyrimidin-4-one, 94. 4-{6-[3-(2-methoxy-pyridin-4yl)-prop-1-ynyl]-4-oxo-4H-pyrido[3,4-d]pyrimidin-3-ylmethyl}-benzoic acid,
95. 3-(4-Methanesulfonyl-benzyl)-6-[3-(2-methoxy-pyridin-4-yl)-prop-1-ynyl)-3H-pyrido[3,4-d]pyrimidin-4-one,
96. 4-{6-[3-(4-methylsulfanyl-phenyl)-prop-1-ynyl]-4-oxo-4H-pyrido[3,4-d]pyrimidin-3-ylmethyl}-benzoic acid,
97. 3-(4-Methanesulfonyl-benzyl)-6-[3-(4-methylsulfanyl-phenyl)-prop-1-ynyl)-3H-pyrido[3,4-d]pyrimidin-4-one,
98. 4-{6-[3-(3-methylsulfanyl-phenyl)-prop-1-ynyl]-4-oxo-4H-pyrido[3,4-d]pyrimidin-3-ylmethyl}-benzoic acid,
99. 3-(4-Methanesulfonyl-benzyl)-6-[3-(3-methylsulfanyl-phenyl)-prop-1-ynyl)-3H-pyrido[3,4-d]pyrimidin-4-one,
100. 4-[4-oxo-6-(3-p-tolyl-prop-1-ynyl)-4H-pyrido[3,4-d]pyrimidin-3-ylmethyl]-benzoic acid,
101. 3-(4-Methanesulfonyl-benzyl)-6-(3-p-tolyl-prop-1-ynyl)-3H-pyrido[3,4-d]pyrimidin-4-one,
102. 4-[4-oxo-6-(3-m-tolyl-prop-1-ynyl)-4H-pyrido[3,4-d]pyrimidin-3-ylmethyl]-benzoic acid,
103. and 3-(4-Methanesulfonyl-benzyl)-6-(3-m-tolyl-prop-1-ynyl)-3H-pyrido[3,4-d]pyrimidin-4-one.

Examples 104 and 105

These compounds are obtained according to the procedure described in Examples 14 and 21 using the corresponding substrates and reagents.
104. 3-(3,4-Difluoro-benzyl)-4-oxo-3,4-dihydro-quinazoline-6-carboxylic acid (2-methoxy-pyridin-4-ylmethyl)-amide
105. 3-(3,4-Difluoro-benzyl)-4-oxo-3,4-dihydro-quinazoline-6-carboxylic acid 4-methoxy-benzylamide

PHARMACOLOGICAL STUDIES OF COMPOUNDS OF THE INVENTION

Example 106: Evaluation of the in vitro activity of the MMP-13 inhibitor compounds according to the invention.

The inhibitory activity of the compounds of formula (I) according to the invention with respect to matrix metalloprotease-13 is evaluated by testing the ability of the compounds of the invention to inhibit the proteolysis of a peptide substrate with MMP-13.

The peptide substrate used in the test is the following peptide: Ac-Pro-Leu-Gly-thioester-Leu-Leu-Gly-OEt.

The inhibitory activity of a compound of formula (I) according to the invention is expressed as the $IC_{50}$ value, which is the concentration of inhibitor for which an inhibition of 50% of the activity of the matrix metalloprotease under consideration is observed.

To carry out this test, a reaction medium of 100 $\mu$l volume is prepared, containing: 50 mM of HEPES buffer, 10 mM of $CaCl_2$ and 1 mM of 5,5'-dithiobis-(2-nitrobenzoic acid) (DTNB), and 100 $\mu$M of substrate, the pH being adjusted to 7.0.

Increasing concentrations of the inhibitory compound present in a 2.0% DMSO solution and 2.5 nM of the catalytic domain of human MMP-13 are added to the test samples.

The concentrations of inhibitors present in the test samples range from 100 $\mu$M to 0.5 nM. The measurement of the proteolysis of the substrate peptide is monitored by measuring the absorbence at 405 nm using a spectrophotometer for reading microplates, at the laboratory temperature, the measurements being carried out continuously for 10 to 15 minutes.

The $IC_{50}$ values are calculated from a curve in which the percentage of the catalytic activity relative to the control is represented on the X-axis and the concentration of inhibitor is represented on the Y-axis.

The $IC_{50}$ values on MMP-13 of the compounds of Examples 1 to 10, 14–19, 21, 23–25, 58–60, 62, 64–71, 104, 105 are all below 1 $\mu$M.

The test described above for the inhibition of MMP-13 was also adapted and used to determine the ability of the compounds of formula (I) to inhibit the matrix metalloproteases MMP-1, MMP-2, MMP-3, MMP-7, MMP-9, MMP-12 and MMP-14.

The results obtained show that the compounds according to the invention generally have $IC_{50}$ values for MMP-13 which are about 100 times lower than the $IC_{50}$ values for the same compounds with respect to the other matrix metalloproteases tested.

What is claimed is:

1. A compound selected from those of formula (I):

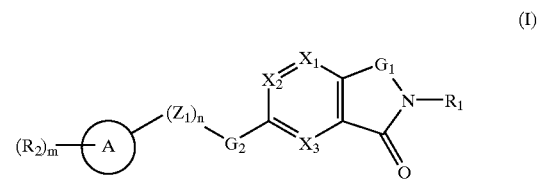

(I)

wherein:

One of $X_1$, $X_2$, and $X_3$ is a nitrogen atom and the other two, independently of each other, represent a group —$CR_3$ in which $R_3$ represents a group selected from hydrogen, ($C_1$–$C_6$)alkyl, amino, mono($C_1$–$C_6$)alkylamino, di($C_1$–$C_6$)alkylamino, hydroxy, ($C_1$–$C_6$)alkoxy, and halogen, $G_1$ represents a group selected from those of formulae (i/a) and (i/b):

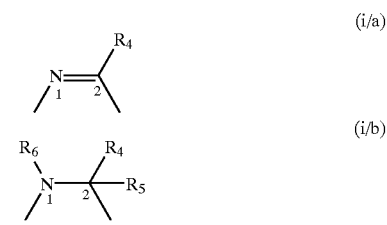

in which:
the carbon atom with number 2 is attached to the group N—$R_1$ in the ring,
$R_4$ and $R_5$, identical or different, independently of each other, represent a group selected from hydrogen, ($C_1$–$C_6$)alkyl, aryl, aryl($C_1$–$C_6$)alkyl, cycloalkyl, cycloalkyl($C_1$–$C_6$)alkyl, heteroaryl, heteroaryl($C_1$–$C_6$)alkyl, heterocycloalkyl, and heterocycloalkyl($C_1$–$C_6$)alkyl,
$R_6$ represents a group selected from:
hydrogen, trifluoromethyl, $OR_7$, $NR_7R_8$, in which $R_7$ and $R_8$, identical or different independently of each other, represent hydrogen or ($C_1$–$C_6$)alkyl,
($C_1$–$C_6$)alkyl, ($C_2$–$C_6$)alkenyl, ($C_2$–$C_6$)alkynyl, aryl, aryl($C_1$–$C_6$)alkyl, cycloalkyl($C_1$–$C_6$)alkyl, heteroaryl, heteroaryl($C_1$–$C_6$)alkyl, heterocycloalkyl, and heterocycloalkyl($C_1$–$C_6$)alkyl, these groups being optionally substituted by one or more groups, which may be identical or different independently of each other, selected from halogen, amino, mono($C_1$–$C_6$)alkylamino, di($C_1$–$C_6$)alkylamino, each alkyl moiety being identical or different independently of each other, cyano, trihalogeno($C_1$–$C_6$)alkyl, ($C_1$–$C_6$)acyl, —C(=O)O$R_7$, —O$R_7$ and —S$R_7$, in which $R_7$ is as defined hereinbefore, $G_2$ represents a group selected from carbon—carbon triple bond, —CH=C=CH—, C=O, C=S, S(O)$_{n1}$ in which n1 represents an integer from 0 to 2 inclusive, and a group of formula (i/c):

in which the carbon atom with number 1 is attached to the bicycle of the compound of formula (1), $Y_1$ represents a group selected from oxygen, sulphur, —NH and —N($C_1$–$C_6$)alkyl, and $Y_2$ represents a group selected from oxygen, sulphur, —NH and —N($C_1$–$C_6$)alkyl, n represents an integer from 0 to 6 inclusive, $Z_1$ represents —C$R_9R_{10}$, wherein $R_9$ and $R_{10}$, identical or different independently of each other, represent a group selected from hydrogen, ($C_1$–$C_6$)alkyl, trihalogeno ($C_1$–$C_6$)alkyl, halogen, —O$R_7$, —S$R_7$, and —C(=O)O$R_7$, in which $R_7$ is as defined hereinbefore, amino, mono($C_1$–$C_6$)alkylamino, di($C_1$–$C_6$)alkylamino in which each alkyl moiety is identical or different independently of each other, and wherein when n is greater than or equal to 2, the hydrocarbon chain $Z_1$ optionally contains one to two isolated or conjugated multiple bonds, and/or wherein when n is greater than or equal to 2, one of said —C$R_9R_{10}$ may optionally be replaced with a group selected from oxygen, S(O)$_{n1}$ in which n1 is as defined hereinbefore, —NH and —N($C_1$–$C_6$)alkyl, A represents a group selected from aryl, heteroaryl, cycloalkyl, and heterocycloalkyl, these groups being 5- or 6-membered monocycle or bicycle composed of two 5- or 6-membered monocycle, $R_1$ represents a group selected from:
hydrogen,
($C_1$–$C_6$)alkyl, ($C_2$–$C_6$)alkenyl, ($C_2$–$C_6$)alkynyl, these groups may be optionally substituted with one or more groups, which may be identical or different independently of each other, selected from amino, cyano, trihalogeno($C_1$–$C_6$)alkyl, cycloalkyl, —C(=O)N$R_7R_8$, —C(=O)O$R_8$, O$R_8$, S$R_8$, in which $R_7$ and $R_8$, which may be identical or different independently of each other, represent hydrogen or ($C_1$–$C_6$)alkyl,
and the group of formula (i/d):

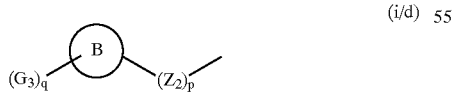

in which p is an integer from 0 to 8 inclusive,
$Z_2$ represents —C$R_{11}R_{12}$ wherein $R_{11}$ and $R_{12}$, identical or different independently of each other, represent a group selected from hydrogen, ($C_1$–$C_6$)alkyl, phenyl, trihalogeno($C_1$–$C_6$)alkyl, halogen, amino, O$R_7$, S$R_7$ and —C(=O)O$R_7$ in which $R_7$ represents hydrogen or ($C_1$–$C_6$)alkyl, and wherein when p is greater than or equal to 2, the hydrocarbon chain $Z_2$ optionally contains one or two isolated or conjugated multiple bonds, and/or wherein n is greater than or equal to 2, one of said —C$R_{11}R_{12}$ may optionally be replaced with a group selected from oxygen, S(O)$_{n1}$ in which n1 is as defined hereinbefore, —NH, —N($C_1$–$C_6$)alkyl, and carbonyl, B represents a group selected from aryl, heteroaryl, cycloalkyl, and heterocycloalkyl, these groups being 5- or 6-membered monocycle or bicycle composed of two 5- or 6- membered monocycle, q is an integer from 0 to 7 inclusive, the group(s) $G_3$, which may be identical or different independently of each other, is (are) selected from ($C_1$–$C_6$)alkyl, halogen, CN, $NO_2$, $CF_3$, $OCF_3$, —(C$H_2$)$_k$N$R_{13}R_{14}$, —N($R_{13}$)C(=O)$R_{14}$, —N($R_{13}$)C(=O)O$R_{14}$, —N($R_{13}$)S$O_2R_{14}$, —N(S$O_2R_{13}$)$_2$, —O$R_{13}$, —S(O)$_{k1}R_{13}$, —S$O_2$—N($R_{13}$)—(C$H_2$)$_{k2}$—N$R_{14}R_{15}$, —(C$H_2$)$_k$S$O_2$N$R_{13}R_{14}$, -$X_4$C$H_2$)$_k$C(=O)O$R_{13}$, —(C$H_2$)$_k$C(=O)O$R_{13}$, —C(=O)O—(C$H_2$)$_{k2}$—N$R_{13}R_{14}$, —C(=O)O—(C$H_2$)$_{k2}$—C(=O)O$R_{16}$, -$X_4$(C$H_2$)$_k$C(=O)N$R_{13}R_{14}$, —(C$H_2$)$_k$C(=O)N$R_{13}R_{14}$, —$R_{17}$—C(=O)O$R_{13}$, -$X_5$—$R_{18}$, and —C(=O)—$R_{19}$—N$R_{13}R_{14}$ in which:

$X_4$ represents a group selected from oxygen atom, sulphur atom optionally substituted by one or two oxygen atoms, and nitrogen atom substituted by a hydrogen atom or a ($C_1$–$C_6$)alkyl group, k is an integer from 0 to 3 inclusive, k1 is an integer from 0 to 2 inclusive, k2 is an integer from 1 to 4 inclusive, $R_{13}$, $R_{14}$ and $R_{15}$, which may be identical or different independently of each other, are selected from hydrogen and ($C_1$–$C_6$)alkyl, $R_{16}$ represents a group selected from ($C_1$–$C_6$)alkyl, —$R_{19}$—N$R_{13}R_{14}$, —$R_{19}$—N$R_{13}$—C(=O)—$R_{19}$—N$R_{14}R_{15}$, and —C(=O)O—$R_{19}$—N$R_{13}R_{14}$ in which $R_{19}$ represents a linear or branched ($C_1$–$C_6$) alkylene group, and $R_{13}$, $R_{14}$ and $R_{15}$ are as defined hereinbefore, $R_{17}$ represents a ($C_3$–$C_6$)cycloalkyl group, $X_5$ represents a group selected from single bond, —C$H_2$—, oxygen atom, sulphur atom optionally substituted by one or two oxygen atoms, and nitrogen atom substituted by hydrogen atom or ($C_1$–$C_6$) alkyl group, $R_{18}$ represents a group selected from:
5- or 6-membered monocycle aryl, heteroaryl, which is optionally substituted by one or more groups, which may be identical or different, selected from ($C_1$–$C_6$)alkyl, halogen, hydroxy, cyano, tetrazolyl, amino, and —C(=O)O$R_7$ wherein $R_7$ represents hydrogen or ($C_1$–$C_6$)alkyl,
and 5- or 6-membered monocycle cycloalkyl, heterocycloalkyl, which is optionally substituted by one or more groups, which may be identical or different, selected from ($C_1$–$C_6$)alkyl, halogen, hydroxy, oxo, cyano, tetrazolyl, amino, and —C(=O)O$R_7$ wherein $R_7$ represents hydrogen or ($C_1$–$C_6$)alkyl, m is an integer from 0 to 7 inclusive, the group(s) $R_2$, which may be identical or different independently of each other, is (are) selected from ($C_1$–$C_6$)alkyl, halogen, —CN, $NO_2$, $SCF_3$, —$CF_3$, —$OCF_3$, —N$R_7R_8$, —O$R_8$, —S$R_8$, —SO$R_8$, —SO$_2$R$_8$, —(CH$_2$)$_k$SO$_2$NR$_7$R$_8$, -X$_7$(CH$_2$)$_k$C(=O)OR$_8$, —(CH$_2$)$_k$C(=O)OR$_8$, -X$_7$(CH$_2$)$_k$C(=O)NR$_7$R$_8$, —(CH$_2$)$_k$C(O)NR$_7$R$_8$, and -X$_8$—R$_{20}$ in which:

X$_7$ represents a group selected from oxygen, sulphur optionally substituted by one or two oxygen atoms, and nitrogen substituted by hydrogen or (C$_1$–C$_6$) alkyl, k is an integer from 0 to 3 inclusive, R$_7$ and R$_8$, which may be identical or different independently of each other, are selected from hydrogen and (C$_1$–C$_6$)alkyl, X$_8$ represents a group selected from single bond, —CH$_2$—, oxygen atom, sulphur atom optionally substituted by one or two oxygen atoms, and nitrogen atom substituted by hydrogen atom or (C$_1$–C$_6$) alkyl group, R$_{20}$ represents 5- or 6-membered monocycle aryl, heteroaryl, cycloalkyl, or heterocycloalkyl which is optionally substituted by one or more groups, which may be identical or different, selected from (C$_1$–C$_6$) alkyl, halogen, hydroxy and amino, and when the ring is heterocyclic, it comprises from 1 to 4 heteroatoms selected from nitrogen, oxygen and sulphur, optionally, the racemic forms thereof, isomers thereof, N-oxides thereof, and the pharmaceutically acceptable salts thereof, it being understood that when no specification are described:

an aryl group denotes an aromatic monocyclic or bicyclic system containing from 5 to 10 carbon atoms, and in the case of a bicyclic system, one of the ring of which is aromatic in character, and the other ring of which may be aromatic or partially hydrogenated, a heteroaryl group denotes an aryl group as described above in which 1 to 4 carbon atoms are replaced by 1 to 4 hetero atoms selected from oxygen, sulfur and nitrogen, a cycloalkyl group denotes a monocyclic or bicyclic system containing from 3 to 10 carbon atoms, this system being saturated or partially unsaturated but without aromatic character, and a heterocycloalkyl group denotes a cycloalkyl group as defined hereinbefore in which 1 to 4 carbon atoms are replaced by 1 to 4 hetero atoms selected from oxygen, sulfur, and nitrogen.

2. A compound according to claim 1 wherein:

G$_2$ represents a group selected from C=O, C=S, S(O)$_{n1}$ in which n1 represents an integer from 0 to 2 inclusive, or a group of formula (i/c):

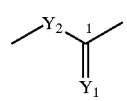

(i/c)

in which the carbon atom with number 1 is attached to the bicycle of the compound of formula (I), Y$_1$ represents a group selected from oxygen, sulphur, —NH and —N(C$_1$–C$_6$)alkyl, and Y$_2$ represents a group selected from oxygen, sulphur, —NH and —N(C$_1$–C$_6$)alkyl, X$_1$, X$_2$, X$_3$, G$_1$, n, Z$_1$, A, R$_1$, m and R$_2$ are as defined in formula (I), optionally, the racemic forms thereof, isomers thereof, N-oxides thereof, and the pharmaceutically acceptable salts thereof.

3. A compound according to claim 1 wherein:

G$_2$ represents a carbon—carbon triple bond, n represents an integer from 1 to 6 inclusive, X$_1$, X$_2$, X$_3$, G$_1$, Z$_1$, A, R$_1$, m and R$_2$ are as defined in formula (I), optionally, the racemic forms thereof, isomers thereof, N-oxides thereof, and the pharmaceutically acceptable salts thereof.

4. The compound according to claim 1, wherein X$_2$ is nitrogen and X$_1$ and X$_3$, independently of each other, represent a group —CR$_3$ in which R$_3$ represents a group selected from hydrogen, (C$_1$–C$_6$)alkyl, amino, mono (C$_1$–C$_6$)alkylamino, di(C$_1$–C$_6$)alkylamino, hydroxy, (C$_1$–C$_6$)alkoxy, and halogen.

5. The compound according to claim 1, wherein:

G$_1$ represents a group of formula (i/a) in which R$_4$ represents a hydrogen atom or a methyl group, or a group of formula (i/b) in which R$_4$ and R$_5$, identical, represent each a hydrogen atom or a methyl group, and R$_6$ represents a hydrogen atom or a methyl group.

6. The compound according to claim 1, wherein:

G$_2$ represents a carbon—carbon triple bond or a group of formula (i/c) in which Y$_1$ represents an oxygen atom, and Y$_2$ represents a group —NH.

7. The compound according to claim 1, wherein:

R$_1$ is the group of formula (i/d):

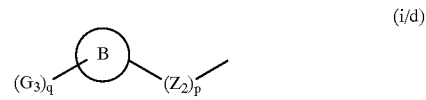

(i/d)

wherein B represents a phenyl group, q is equal to 0 or 1, and G$_3$, when it is present, represents a group selected from OR$_{13}$, halogen, S(O)$_{k1}$R$_{13}$ and (CH$_2$)$_k$C(O)OR$_{13}$ in which R$_{13}$ represents an hydrogen atom or a (C$_1$–C$_6$) alkyl group, k is zero, and k$_1$ is two, and Z$_2$ and p are as defined in claim 1.

8. The compound according to claim 1, wherein:

A represents a group selected from phenyl and pyridyl, m is zero or one, and R$_2$ represents a (C$_1$–C$_6$)alkoxy group or a hydrogen atom.

9. The compound according to claim 1, wherein:

Z$_1$ represents —CR$_9$R$_{10}$ in which R$_9$ and R$_{10}$ represent each a hydrogen atom, and n is one.

10. The compound according to claim 1, wherein:

X$_2$ is nitrogen and X$_1$ and X$_3$, independently of each other, represent a group —CR$_3$ in which R$_3$ represents a group selected from hydrogen, (C$_1$–C$_6$)alkyl, amino, mono(C$_1$–C$_6$)alkylamnino, di(C$_1$–C$_6$)alkylamino, hydroxy, (C$_1$–C$_6$)alkoxy, and halogen;

G$_1$ represents a group selected from those of formulae (i/a):

(i/a)

in which:

the carbon atom with number 2 is attached to the group N—R$_1$ in the ring, and

R$_4$ represents a group selected from hydrogen, (C$_1$–C$_6$) alkyl, aryl, aryl(C$_1$–C$_6$)alkyl, cycloalkyl, cycloalkyl (C$_1$–C$_6$)alkyl, heteroaryl, heteroaryl(C$_1$–C$_6$)alkyl, heterocycloalkyl, and heterocycloalkyl(C$_1$–C$_6$)alkyl;

$G_2$ represents a carbon—carbon triple bond or a group of formula (i/c):

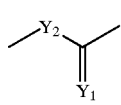

(i/c)

in which the carbon atom with number 1 is attached to the bicycle of the compound of formula (I), $Y_1$ represents oxygen, and $Y_2$ represents —NH;

$R_1$ is the group of formula (i/d):

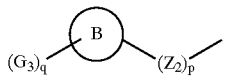

(i/d)

wherein B represents a phenyl group, q is equal to 0 or 1, and $G_3$, when it is present, represents a group selected from $OR_{13}$, halogen, $S(O)_{k_1}R_{13}$ and $(CH_2)_kC(=O)OR_{13}$ in which $R_{13}$ represents an hydrogen atom or a $(C_1-C_6)$alkyl group, k is zero, and $k_1$ is two, and $Z_2$ and p are as defined in the compound of formula (I);

A represents a group selected from phenyl and pyridyl, m is zero or one, and $R_2$ represents a $(C_1-C_6)$alkoxy group or a hydrogen atom; and $Z_1$ represents —$CR_9R_{10}$ in which $R_9$ and $R_{10}$ represent each a hydrogen atom, and n is one.

11. A compound according to claim 1, which is selected from:

3-(3-fluoro-benzyl)-4-oxo-3,4-dihydro-pyrido[3,4-d]pyrimidine-6-carboxylic acid 3-methoxy-benzylamide, and 3-(3-fluoro-benzyl)-4-oxo-3,4-dihydro-pyrido[3,4-d]pyrimidine-6-carboxylic acid 4-methoxy-benzylamide.

12. A compound according to claim 1, which is selected from:

3-(4-fluorobenzyl)-6-(3-phenyl-prop-1-ynyl)-3H-pyrido[3,4-d]pyrimidin-4-one, methyl 4-[6-(3-phenyl-prop-1-ynyl)-4-oxo-4H-pyrido[3,4-d]pyrimidin-3-ylmethyl]-benzoate, and 4-[6-(3-phenyl-prop-1ynyl)-4-oxo-4H-pyrido[3,4-d]pyrimidin-3-ylmethyl]-benzoic acid.

13. A pharmaceutical composition, comprising as active ingredient an effective amount of a compound as claimed in claim 1, in combination with a pharmaceutically-acceptable excipient or carrier.

14. A method for treating a living body afflicted with a disease selected from arthritis, rheumatoid arthritis and osteoarthritis, comprising the step of administering to the living body an amount of a compound of claim 1 which is effective for alleviation of said disease.

15. The method according to claim 14, wherein the disease is arthritis.

16. The method according to claim 14, wherein the disease is osteoarthritis.

17. The method according to claim 14, wherein the disease is rheumatoid arthritis.

* * * * *